(12) United States Patent
Stanton et al.

(10) Patent No.: US 10,265,056 B2
(45) Date of Patent: Apr. 23, 2019

(54) MEDICAL DEVICE HAVING A TENSIONABLE COUPLING

(71) Applicants: Larry Stanton, Burlington, MA (US); John Golden, Norton, MA (US); Gary Kappel, Acton, MA (US); Mark Wood, Shrewsbury, MA (US); Bernadette Durr, Marlborough, MA (US); Brandon Zalewski, Clinton, MA (US); Kenneth Keene, Winchester, MA (US); Barry Weitzner, Acton, MA (US); Paul Smith, Smithfield, RI (US); Naroun Suon, Lawrence, MA (US)

(72) Inventors: Larry Stanton, Burlington, MA (US); John Golden, Norton, MA (US); Gary Kappel, Acton, MA (US); Mark Wood, Shrewsbury, MA (US); Bernadette Durr, Marlborough, MA (US); Brandon Zalewski, Clinton, MA (US); Kenneth Keene, Winchester, MA (US); Barry Weitzner, Acton, MA (US); Paul Smith, Smithfield, RI (US); Naroun Suon, Lawrence, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1787 days.

(21) Appl. No.: 13/755,299

(22) Filed: Jan. 31, 2013

(65) Prior Publication Data

US 2013/0197490 A1    Aug. 1, 2013

Related U.S. Application Data

(60) Provisional application No. 61/592,915, filed on Jan. 31, 2012.

(51) Int. Cl.
A61B 17/00 (2006.01)

(52) U.S. Cl.
CPC ........ *A61B 17/00* (2013.01); *A61B 17/00234* (2013.01); *A61B 2017/00323* (2013.01)

(58) Field of Classification Search
CPC .......... A61M 25/0105; A61M 25/0133; A61M 25/0136; A61M 25/0147;
(Continued)

(56) References Cited

U.S. PATENT DOCUMENTS 5,190,050 A * 3/1993 Nitzsche ........... A61M 25/0136
600/585
5,618,294 A    4/1997 Aust et al.
(Continued)

FOREIGN PATENT DOCUMENTS

WO    WO 2008/067557 A2    6/2008

OTHER PUBLICATIONS

Partial International Search Report for International Application No. PCT/US2013/024020, dated Apr. 25, 2013, 4 pgs.

*Primary Examiner* — Gary Jackson
*Assistant Examiner* — Sebastian X Lukjan
(74) *Attorney, Agent, or Firm* — Bookoff McAndrews, PLLC

(57) ABSTRACT

This invention is directed to a medical device having an elongate shaft having a distal end and a controller coupled to the shaft. A control member can extend through at least part of the elongate shaft and at least part of the controller, wherein the control member in a tensioned configuration can be moveable by the controller to control the distal end of the shaft and the control member can be slack in an untensioned configuration. A tensioning mechanism can be configured to move relative to at least one of the elongate shaft and the controller to tension the control member and automatically lock the control member in the tensioned configuration.

27 Claims, 22 Drawing Sheets

(58) Field of Classification Search
CPC .... A61M 2025/015; A61M 2025/0161; A61M 2017/2902; A61M 2017/2903; A61M 2017/2909; A61M 2017/2901; A61M 2017/291; A61M 2017/2912; A61M 2017/2911; A61M 2017/2925; A61M 2017/2946; A61M 2017/2947; A61B 17/00; A61B 19/22; A61B 17/0023; A61B 2017/00292; A61B 2017/003; A61B 2017/00323; A61B 2017/0023
USPC .............................................................. 606/1
See application file for complete search history.

(56) References Cited

U.S. PATENT DOCUMENTS

| | | | |
|---|---|---|---|
| 5,766,196 A | 6/1998 | Griffiths | |
| 5,891,088 A * | 4/1999 | Thompson | A61M 25/0136 604/524 |
| 2007/0276430 A1 | 11/2007 | Lee et al. | |
| 2008/0015631 A1 * | 1/2008 | Lee | A61B 17/062 606/205 |
| 2008/0058595 A1 * | 3/2008 | Snoke | A61B 1/00135 600/114 |
| 2008/0188868 A1 | 8/2008 | Weitzner et al. | |
| 2008/0255420 A1 * | 10/2008 | Lee | A61B 17/2909 600/137 |
| 2008/0287862 A1 * | 11/2008 | Weitzner | A61M 25/0136 604/28 |
| 2008/0312506 A1 * | 12/2008 | Spivey | A61B 1/00133 600/149 |
| 2011/0184459 A1 * | 7/2011 | Malkowski | A61B 17/29 606/206 |
| 2011/0313506 A1 * | 12/2011 | Ray | A61B 17/12022 623/1.12 |
| 2012/0143088 A1 * | 6/2012 | Schultz | A61B 5/6852 600/585 |
| 2012/0253131 A1 * | 10/2012 | Malkowski | A61B 17/3421 600/201 |

* cited by examiner

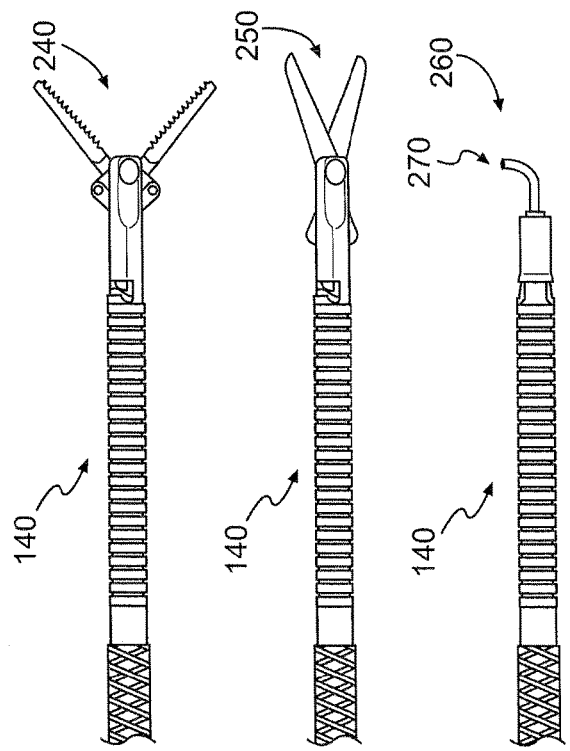
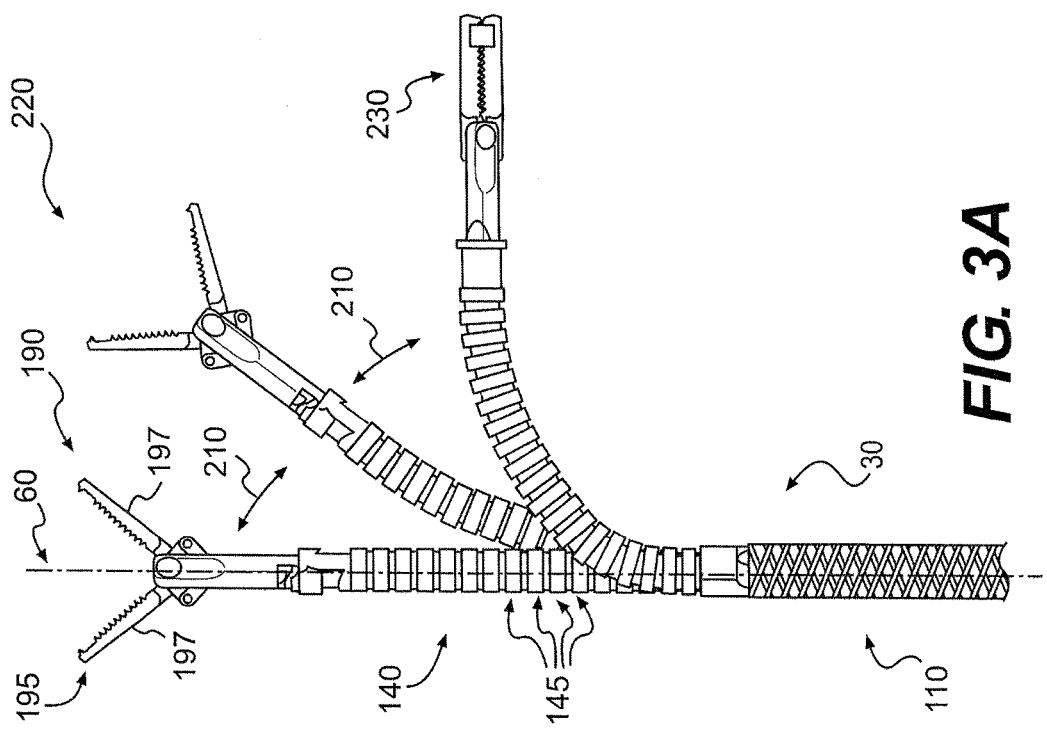
FIG. 3B
FIG. 3A

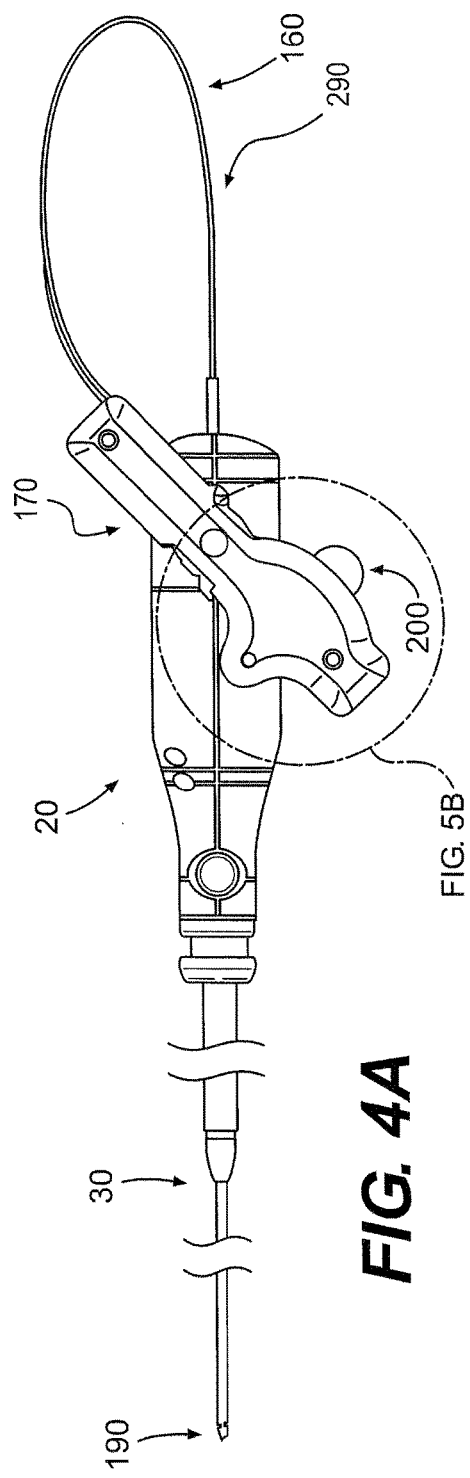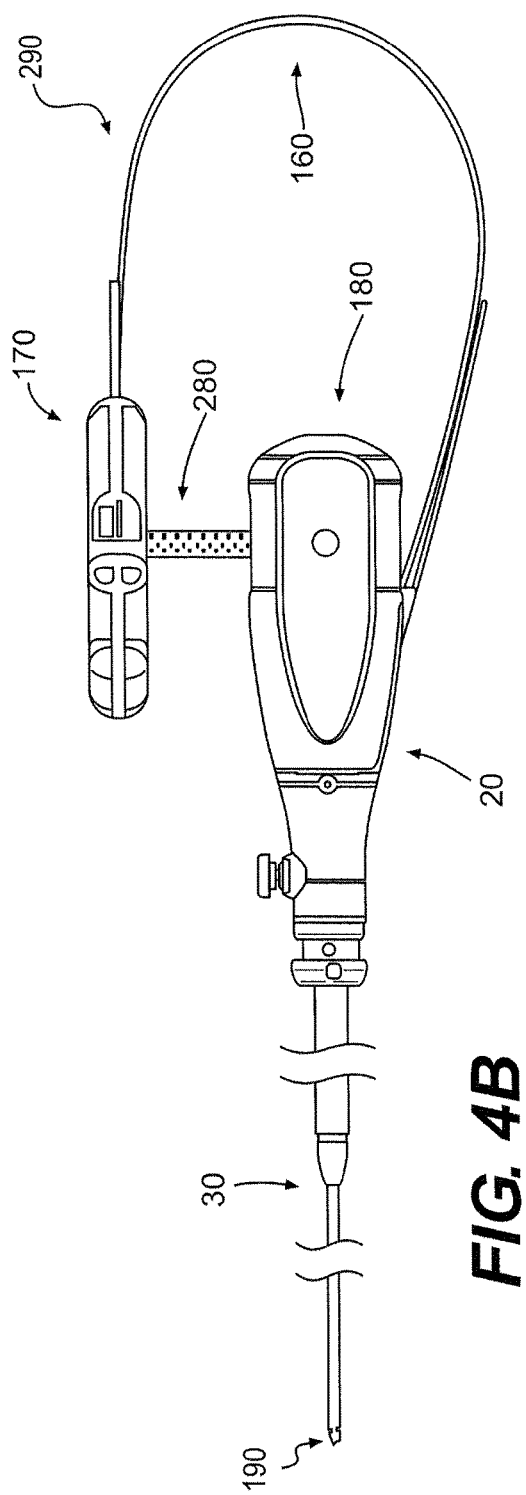

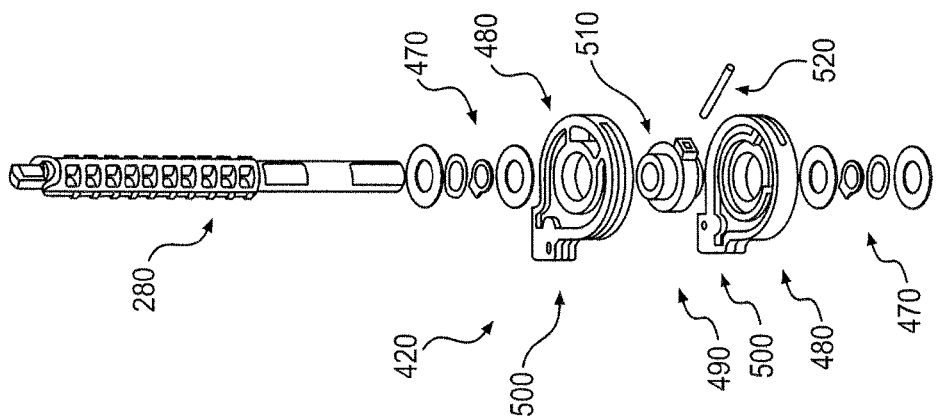
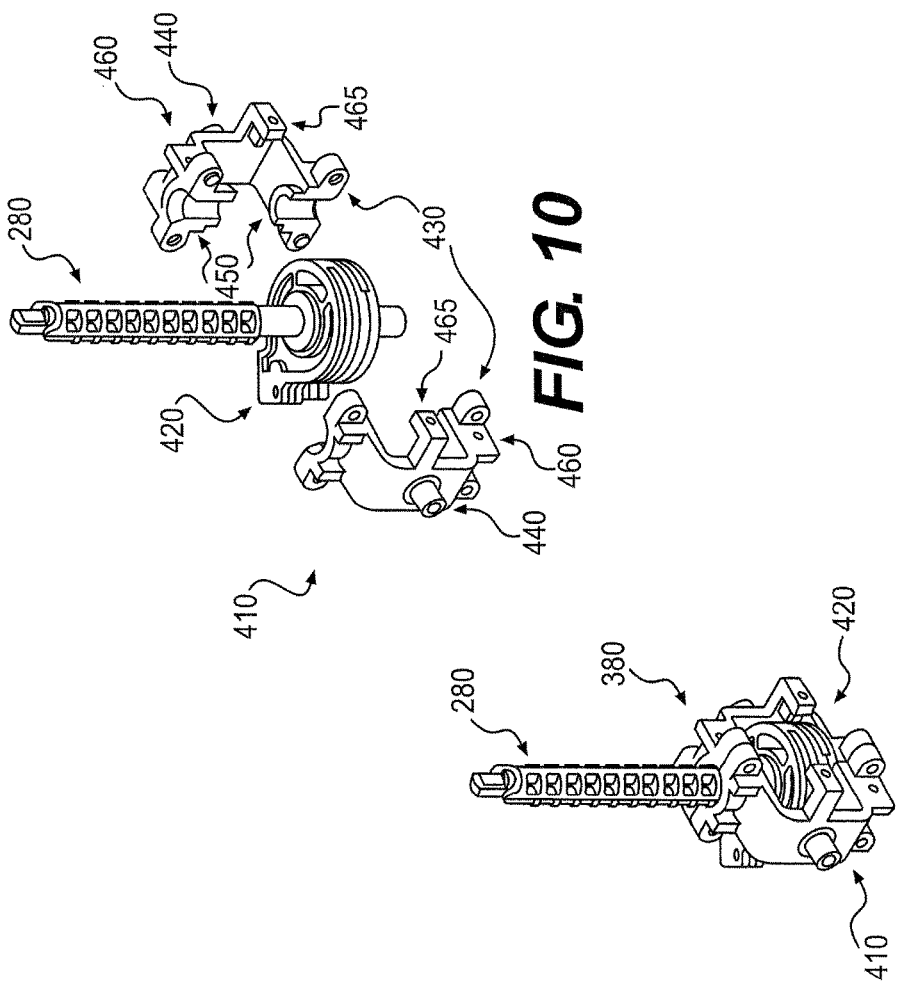

MEDICAL DEVICE HAVING A TENSIONABLE COUPLING

RELATED APPLICATION(S)

This application claims the benefit of priority of U.S. Provisional Application No. 61/592,915 filed Jan. 31, 2012, which is incorporated herein by reference in its entirety.

DESCRIPTION OF THE INVENTION

Field of the Invention

Embodiments of the present invention relate to medical devices. In particular, embodiments of the present invention include a medical device having a tensionable coupling.

Background of the Invention

Minimally invasive surgical tools, such as endoscopic and laparoscopic devices, can provide access to surgical sites while limiting patient trauma. Although the growing capabilities of such therapeutic devices allow physicians to perform an increasing variety of surgeries, improvements are needed to further develop these devices. For example, the performance of some devices can vary if the device has been subjected to temperature or pressure variations.

Some minimally invasive systems use cables, wires, ribbons, rods, or other elongate members to control various device functions, including articulation of a steering section or actuation of an end-effector. These control members may be affected by manufacturing processes, shipping, or storage conditions. For example, contraction or expansion of a control member or a supporting structure can adversely affect device performance. The present invention aims to overcome these and other limitations of conventional devices.

SUMMARY OF THE INVENTION

The medical devices described herein can be provided in an untensioned state and later tensioned for use. Such a tensionable device could be stored or shipped in an untensioned state, and tensioned immediately prior to use by a surgeon. The device may also be configured to automatically lock in the tensioned state or adapted for use with different types of end-effectors. Once locked, an end-effector could be rotated relative to the device to customize the device's orientation.

One aspect of the invention is directed to a medical device having an elongate shaft having a distal end and a controller coupled to the shaft. A control member can extend through at least part of the elongate shaft and at least part of the controller, wherein the control member in a tensioned configuration can be moveable by the controller to control the distal end of the shaft and the control member can be slack in an untensioned configuration. A tensioning mechanism can be configured to move relative to at least one of the elongate shaft and the controller to tension the control member and automatically lock the control member in the tensioned configuration.

According to another aspect, the invention can include a method of pre-tensioning a control member extending within at least part of an elongate shaft and at least part of a controller of a medical device. The method can include mounting a pivot assembly in a fixed position relative to a tensioning fixture, wherein the pivot assembly can be moveably coupled to the controller. The method can also include passing the control member through the pivot assembly, applying a preset tension to the control member, attaching the control member to the pivot assembly, and un-mounting the pivot assembly from the tensioning fixture.

According to another aspect, the invention can include a controller for use with a medical device. The controller can include a base coupled to a catheter configured for use with an endoscopic device and a handle moveably coupled to the base and configured to move a control member to control a distal region of the catheter. The controller can further include a pivot assembly coupling the handle to the base and including a pulley. The pulley can include an attachment mechanism configured to attach the control member to the pulley and permit a proximal region of the control member to extend proximally beyond the pulley and a surface configured to receive a stabilizing member, wherein the stabilizing member can be positionable against the surface to limit movement of the pulley relative to the base and permit application of a select tension to the control member prior to attaching the control member to the pulley.

According to another aspect, the invention can include a method of tensioning and untensioning a medical device. The method can include moving a controller axially relative to a catheter to transition a control member from an untensioned state to a tensioned state and to automatically lock axial movement of the controller and the catheter in the tensioned state, wherein movement of the control member in the tensioned state by the controller can control a distal end of the catheter. The method can also include selectively unlocking axial movement between the controller and the catheter to transition the control member from the tensioned state to the untensioned state.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 3A is a side view of an end-effector articulated in three different positions, according to an exemplary embodiment;

FIG. 3B is a side view of various end-effectors, according to exemplary embodiments;

FIG. 4A is a top view of the device, according to another exemplary embodiment;

FIG. 4B is a side view of the device shown in FIG. 4A;

FIG. 9 is a perspective view of a pivot assembly, according to an exemplary embodiment;

FIG. 10 is a partially exploded view of the pivot assembly shown in FIG. 9;

FIG. 11 is an exploded view of part of the pivot assembly shown in FIG. 9;

DESCRIPTION OF THE EMBODIMENTS

Reference will now be made to exemplary embodiments, examples of which are illustrated in the accompanying drawings. Wherever possible, the same reference numbers will be used throughout the drawings to refer to the same or like parts.

Figure 1:
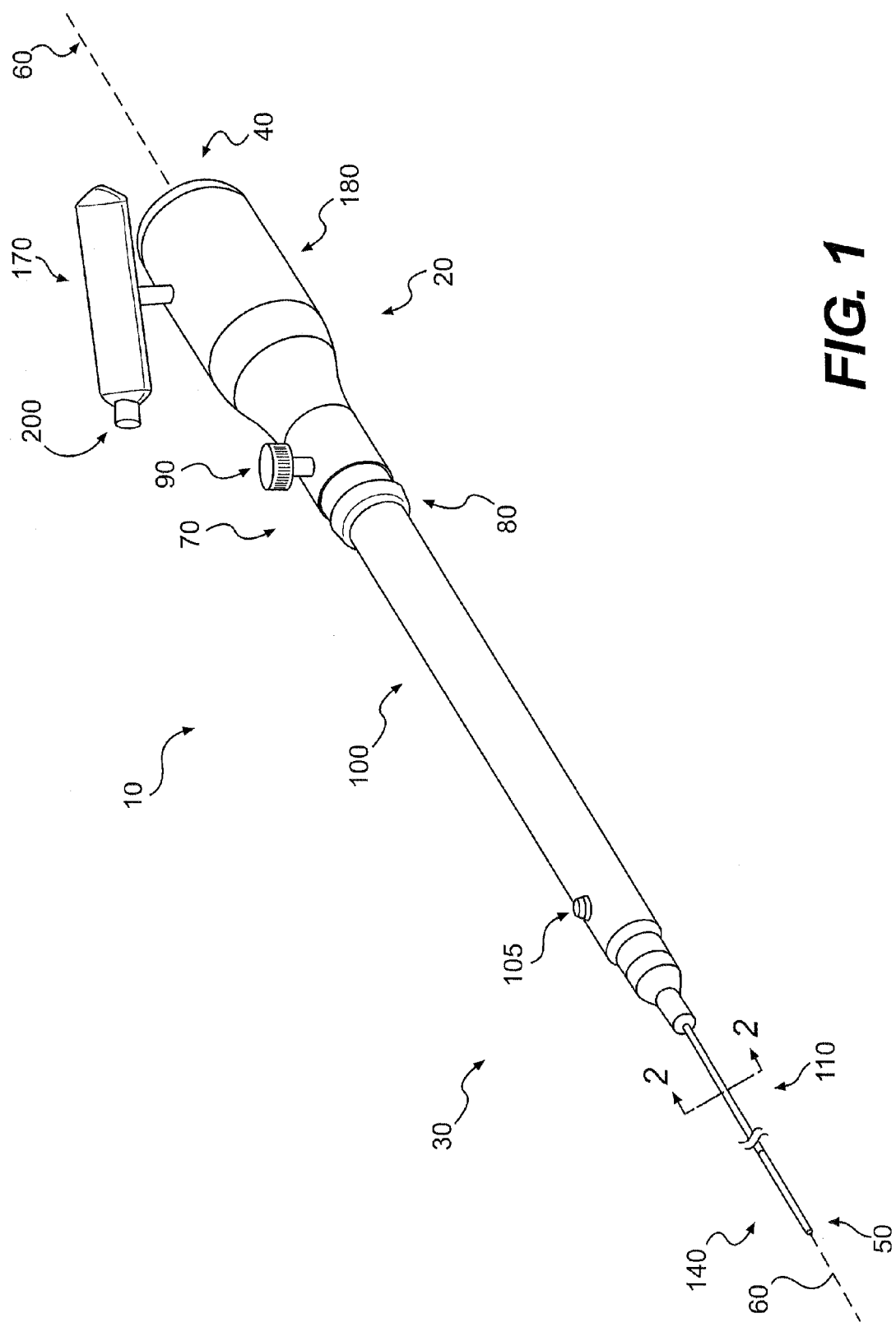
FIG. 1 is perspective view of a device, according to an exemplary embodiment.

FIG. 1 depicts a device 10, according to an exemplary embodiment. Device 10 can include a medical device configured for use with a surgical method, including a therapeutic or diagnostic procedure. For example, device 10 can be configured for use with an endoscope, a guide tube, an access catheter, or other type of device configured to access a patient's body. Device 10 may be used for procedures within or adjacent to various body organs, such as, an esophagus, a heart, a stomach, a pelvic area, a bladder, an intestine, or any other portion of a gastrointestinal, urinary, or pulmonary tract.

Device 10 may be configured for insertion into a patient's body through an anatomical opening. Device 10 may also be used in natural orifice transluminal endoscopic surgery (NOTES) procedures or single incision laparoscopic surgical (SILS) procedures. Accordingly, device 10 can be shaped and sized for placement into a patient via a body cavity or an incision.

As described herein, device 10 can transition from an untensioned configuration to a tensioned configuration. In the tensioned configuration, device 10 can function as required to perform a surgical procedure. In the untensioned configuration, one or more tensionable components of device 10 can be untensioned and may be non-operational. When slack or untensioned, the tensionable components may be subjected to less stress or force than when tensioned. When tensioned, the tensionable components can function as required. In the tensioned state, device 10 can operate optimally. In the untensioned state, device 10 can operate sub-optimally.

As shown in FIG. 1, device 10 can include a controller 20 coupled to and configured to control an elongate shaft 30. Elongate shaft 30 can include a catheter or similar elongate device suitable for use with a surgical procedure. Controller 20 can be moved by a user to control a movement or function of elongate shaft 30. For example, controller 20 can be moved to control forward/backwards, clockwise/counter clockwise, left/right, or up/down movement of elongate shaft 30. Controller 20 can also be configured to control an end-effector (not shown) coupled to elongate shaft 30.

In some embodiments, controller 20 can be moved relative to elongate shaft 30 to transition device 10 from an untensioned configuration to a tensioned configuration. In a tensioned configuration, controller 20 can control elongate shaft 30 as described above. Controller 20 can also be moved relative to elongate shaft 30 to transition device 10 from a tensioned configuration to an untensioned configuration. As described in detail below, these or other components of device 10 can be tensioned in the tensioned configuration and have reduced force applied to them in the untensioned configuration.

Device 10 can have a proximal end 40, a distal end 50, and a longitudinal axis 60. Device 10 can also include a tensioning mechanism 70 configured to tension or untension one or more components of device 10. As shown in FIG. 1, tensioning mechanism 70 can include a rotational knob 80 and a rotational locking mechanism 90. In other aspects, tensioning mechanism 70 could include a button, a bar, a lever, a cam, a rack and a pawl, a collar, a cone, a wedge, a thumb wheel, or other structure to control movement of tensioning mechanism 70 relative to device 10. Tensioning mechanism 70 could move proximally, axially, or rotationally to tension one or more components of device 10.

In some embodiments, knob 80 can be fixedly attached to elongate shaft 30. Knob 80 may move axially along longitudinal axis 60 or rotationally about longitudinal axis 60 relative to controller 20. Consequently, controller 20 may be moved axially, rotationally, or both axially and rotationally relative to elongate shaft 30.

It is also contemplated that knob 80 could be fixedly attached to controller 20, resulting in movement of knob 80 and controller 20 relative to elongate shaft 30. In addition, elongate shaft 30 or controller 20 can include inner or outer components that remain fixed relative to the other component. For example, elongate shaft 30 could include an outer sleeve (not shown) that remains fixed relative to controller 20 as elongate shaft 30 is moved relative to controller 20.

An axial locking mechanism (not shown) may be configured to lock axial movement of controller 20 relative to elongate shaft 30. As described in detail below, this locking may be automated to permit only one-way axial movement of controller 20 relative to elongate shaft 30 along longitudinal axis 60. Automated locking may lock device 10 in the tensioned state.

While locked axially, knob 80 may permit rotational movement of controller 20 relative to elongate shaft 30. This rotational movement may permit relative rotation between controller 20 and an end-effector (not shown) located on elongate shaft 30. Depending on a user's preference, the end-effector may be variously located relative to controller 20. Rotational locking mechanism 90 may be operated to limit rotational movement between controller 20 and elongate shaft 30.

Knob 80 is shown in FIG. 1 as fixedly attached to a proximal region 100 of elongate shaft 30. Proximal region 100 can be rigid or formed of a metal alloy, such as, for example, stainless steel. Proximal region 100 could also include a rigid polymer. Proximal region 100 can also be moveably coupled to a frame (not shown) or system (not shown) to permit movement of device 10 along or about longitudinal axis 60. Exemplary frame and system structures are described in U.S. Patent Application Publication No. 2008/0188868, which is incorporated by reference here in its entirety.

Proximal region 100 may include a disabling mechanism 105 located anywhere on device 10. Disabling mechanism 105 may be activated by sliding proximal region 100 within a bearing tube (not shown) or other structure configured to receive device 10. In some embodiments, disabling mechanism 105 could include a tab, a cone, a rounded surface, or other structure configured to engage the bearing assembly. An exemplary bearing assembly is described in U.S. application Ser. No. 13/297,675, filed Nov. 16, 2011, which is incorporated by reference here in its entirety.

Disabling mechanism 105 could be configured to permit movement of knob 80 or other part of tensioning mechanism 70. For example, depressing disabling mechanism 105 could unlock movement of knob 80 relative to controller 20. Only after positioning device 10 within the bearing assembly could an operator slide knob 80 distally, tensioning device 10. In other embodiments, disabling mechanism 105 could control another function of tensioning mechanism 70 or device 10. For example, disabling mechanism 105 could be moved to operate tensioning mechanism 70. Disabling mechanism 105 could also lock relative movement of controller 20, shaft 30, or another component of device 10.

Figure 2:
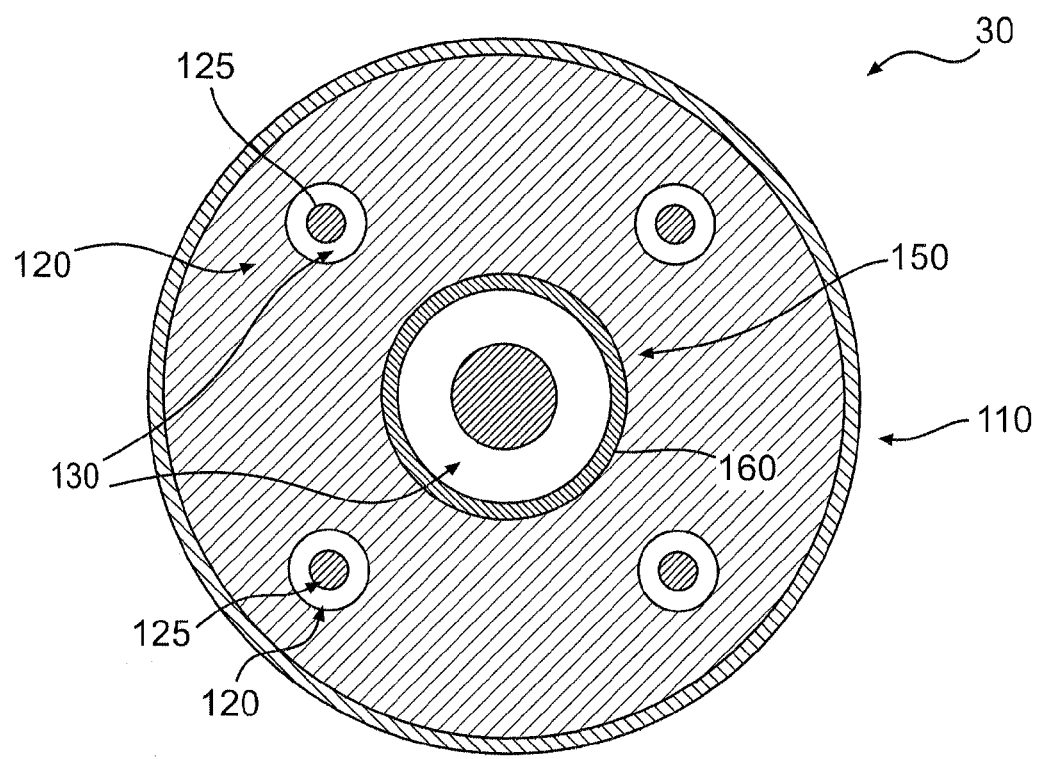
FIG. 2 is a cross-section view of a shaft of a device, according to an exemplary embodiment.

Elongate shaft 30 can also include a distal region 110. Distal region 110 can be flexible and may include one or more lumens 120. As shown in FIG. 2, distal region 110 can include four lumens 120, wherein each lumen 120 is configured to receive an articulation member 125. As explained below, articulation member 125 may be moved to control a steering section 140. Distal region 110 can also include a lumen 150 configured to receive an actuation member 160 configured to actuate an end-effector. For example, articulation member 125 can include a braided metal wire and actuation member 160 can include a Bowden cable. Actuation member 160 can also include an actively conductive wire configured to permit current flow to an instrument, such as, for example, an electrosurgical hook end-effector or electrified scissors.

Device 10 can be configured to mechanically transmit movement or forces from controller 20 to elongate shaft 30 via one or more members 125, 160. At least part of one or more members 125, 160 may extend through controller 20 or elongate shaft 30. One or more articulation members 125 may be moved to articulate one or more parts of elongate shaft 30, such as, for example, steering section 140. One or more actuation members 160 may be moved to actuate one or more end-effectors on elongate shaft 30, such as, for example, to open and close jaw members of a grasper or a dissector.

Figure 5A:
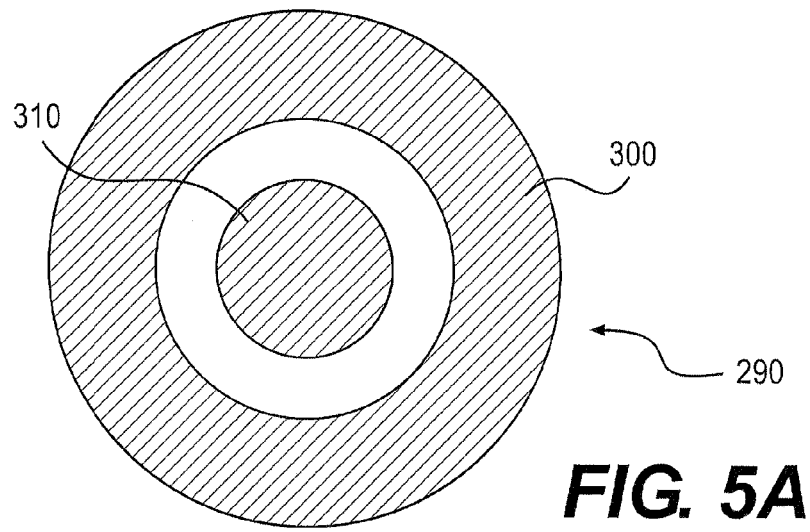
FIG. 5A is a cross-section view of a control member, according to an exemplary embodiment.

Members 125, 160 can include a cable, a wire, a ribbon, a rod, a Bowden cable, or other type of elongate element configured to transfer a movement or a mechanical force. For example, members 125, 160 could include a metal alloy, braided synthetic thread, coil, polymer, or similar flexible material configured to transfer a tensile force. As shown in FIG. 5A, a Bowden cable 290 can include an inner member 310 configured to transfer tensile force and an outer member 300 configured to transfer compressive force. In some embodiments, outer member 300 can include an incompressible helical coil.

Members 125, 160 can be configured to transfer tensile force, compressive force, or both tensile and compressive forces. In addition, member 125, 160 can transfer rotational force or movement. Members 125, 160 may also include one or more types of elongate element and may be mechanically coupled to one or more gears, pulleys, capstans, or other mechanical devices configured to transfer mechanical forces or movement. Further, members 125, 160 may be sized and shaped depending on load requirements and geometric constraints.

Members 125, 160 are described herein as including various features and having various functions. One of ordinary skill will also appreciate that these features and functions may be interchangeable between articulation members 125 and actuation members 160. That is, either articulation member 125 or actuation member 160 could include one or more features or functions ascribed to the other member. For clarity, members 125, 160 will be collectively referred to as control members 130.

As explained below, control members 130 may be selectively tensioned or untensioned. For example, tensioning mechanism 70 can be configured to move to controller 20 relative to elongate shaft 30 to selectively tension one or more control members 130. Further, one or more control members 130 may not be tensioned or untensioned by tensioning mechanism 70. It is also contemplated that one or more control members 130 can tensioned to have different magnitudes of tension. For example, a first control member 130 could be tensioned to 1 lb while a second control member could be tensioned to 2 lb.

As shown in FIG. 1, elongate shaft 30 can include steering section 140 located at or near distal end 50. Steering section 140 can also be located anywhere along distal region 110 or encompass the entire length of distal region 110. To manipulate steering section 140, a user can move controller 20 to selectively move distal end 50 up, down, left, or right.

Controller 20 can include a handle 170 moveably coupled to a base 180. In use, handle 170 can be an actuator configured to receive user inputs. For example, handle 170 could be configured to engage a left hand or a right hand of a user. Handle 170 could include a ridge located to separate two adjacent fingers, a surface conforming to part of a human hand, or an aperture configured to receive two or more digits of a user. An exemplary handle is described in U.S. Patent Application Publication No. 2008/0287862, entitled "Medical device having a modular handle," filed Jan. 31, 2012, both of which are incorporated by reference here in their entirety.

Controller 20 can be configured to provide direct manual user control of elongate shaft 30. Movement of controller 20 along or about longitudinal axis 60 may correspondingly move elongate shaft 30 along or about longitudinal axis 60. Movement of a user's hand may also move handle 170 relative to base 180 to move elongate shaft 30 up, down, left, or right. In other embodiments, controller 20 can include one or more knobs, dials, levers, or other devices configured to control elongate shaft 30.

Handle 170 can also include a trigger 200 configured to actuate an end-effector 190 coupled to elongate shaft 30 (see FIG. 3A). As shown in FIG. 1, trigger 200 can be positioned on handle 170 and configured to be moved by a user's thumb or finger without the user taking their hand off handle 170. Trigger 200 could also be located on base 180.

End-effector 190 is shown in FIG. 3A in three different positions: vertical; forty five degrees relative to vertical; and horizontal. End-effector 190 can be moved as indicated by arrows 210 in various directions relative to longitudinal axis 60 by movement of one or more control members 130 coupled to steering section 140.

In some embodiments, steering section 140 can include a plurality of articulation links 145. Articulation links 145 can be moved relative to adjacent links via a pivot, flexible connection, sliding engagement, bearing, or other type of joint. One or more articulation links 145 can be coupled to one or more control members 130 to control movement of steering section 140. In other embodiments, steering section 140 can be formed from a flexible material. In other embodiments, steering section 140 may comprise a portion of the designed for flexibility, such as, for example, by providing slot, grooves, or holes in the flexible material to provide bending.

In some embodiments, end-effector 190 can include a grasper 195 having one or more movable jaw members 197 hingedly attached to elongate shaft 30. Grasper 195 can be configured to grasp tissue. Jaw members 197 may be actuated to move relative to each other. For example, jaw members 197 can be configured to assume an open configuration 220, a closed configuration 230, or any configuration therebetween.

FIG. 3B depicts various end-effectors configured for use with elongate shaft 30. These and other types of end-effectors may be distally located on elongate shaft 30 and can be articulated, actuated, or both. One or more control members 130 can be moved to control actuation of end-effector 190. And one or more control members 130 can be moved to control articulation of end-effector 190.

A dissector 240 or a pair of scissors 250 can be included on different embodiments of device 10. Both dissector 240 and scissors 250 can include multiple control members 130 configured to provide articulation or actuation of both types of end-effectors. End-effector 190 could also include an electrosurgical hook 260, having a hook 270 configured to apply ablative energy to tissue. Electrosurgical hook 260 may require articulation and may not require actuation. For electrosurgical hook 260, actuation member 160 can include an electrically conductive cable configured to transmit electrical current from controller 20 to hook 270.

These and other end-effectors may operate more effectively if control members 130 for each type of end-effector have a specific tension. For example, scissors 250 may require its actuation member 160 to have less tension than an actuation member 160 for grasper 195. Articulation of grasper 195 may also require more tension than is required for scissors 250. In addition, one or more articulation members 125 may be tensioned differently to provide more responsive movement in, for example, the left/right direction compared with the up/down direction. Various devices and methods for selectively tensioning control members 130 are described below.

FIG. 4A illustrates a top-view of device 10 and FIG. 4B illustrates a side-view of device 10, according to an exemplary embodiment. As shown, actuation member 160 extends from handle 170 to base 180 of controller 20. In other embodiments, actuation member 160 can extend within a shaft 280 that can extend from handle 170 to base 180. Handle 170 may be detachable from shaft 280 and shaft 280 may be moveably coupled to base 180.

Trigger 200 may be mechanically coupled to end-effector 190 at least in part by actuation member 160, wherein at least part of actuation member 160 can include Bowden cable 290. FIG. 5A shows Bowden cable 290 with outer member 300 surrounding inner member 310. Because compressive forces can be transferred through outer member 300 and tensile forces can be transferred through inner member 310, relative movement between outer member 300 and inner member 310 can transfer compressive or tensile forces.

Figure 5B:
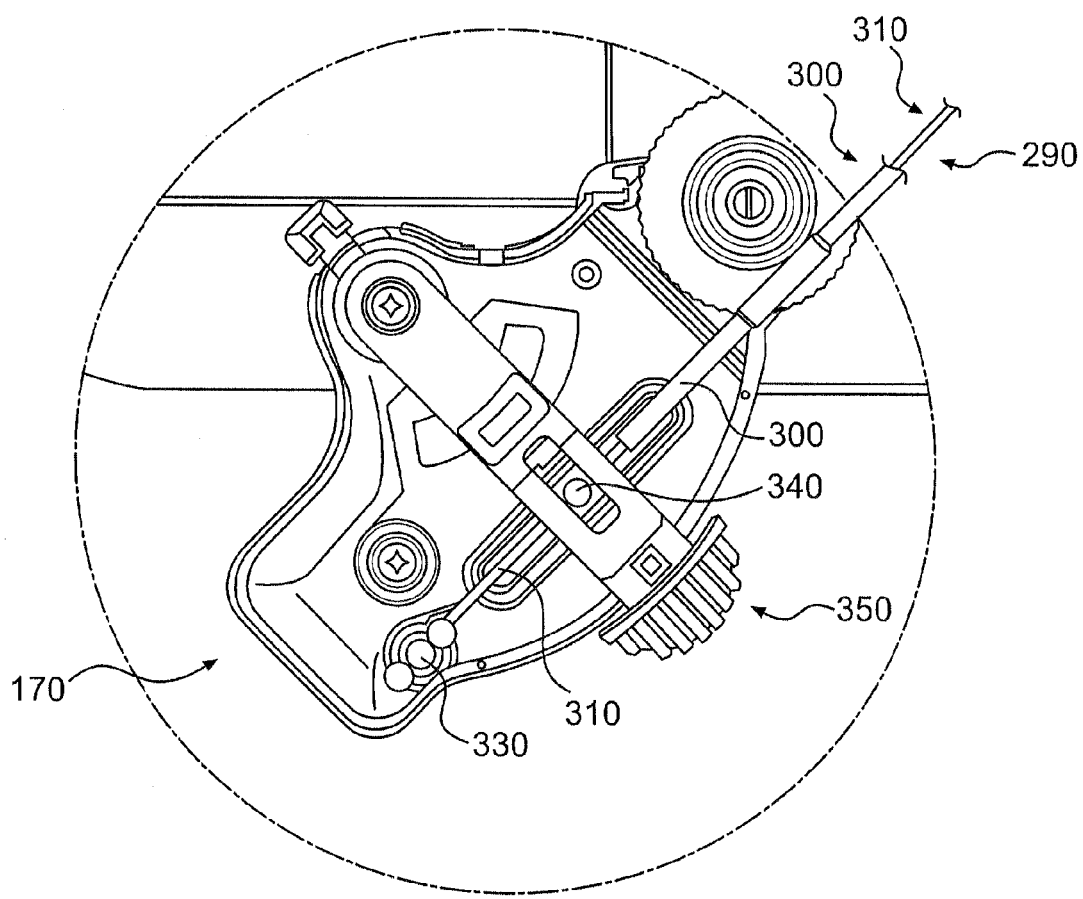
FIG. 5B is a partial cut-away view of a controller of a device, according to an exemplary embodiment.
Figure 6:
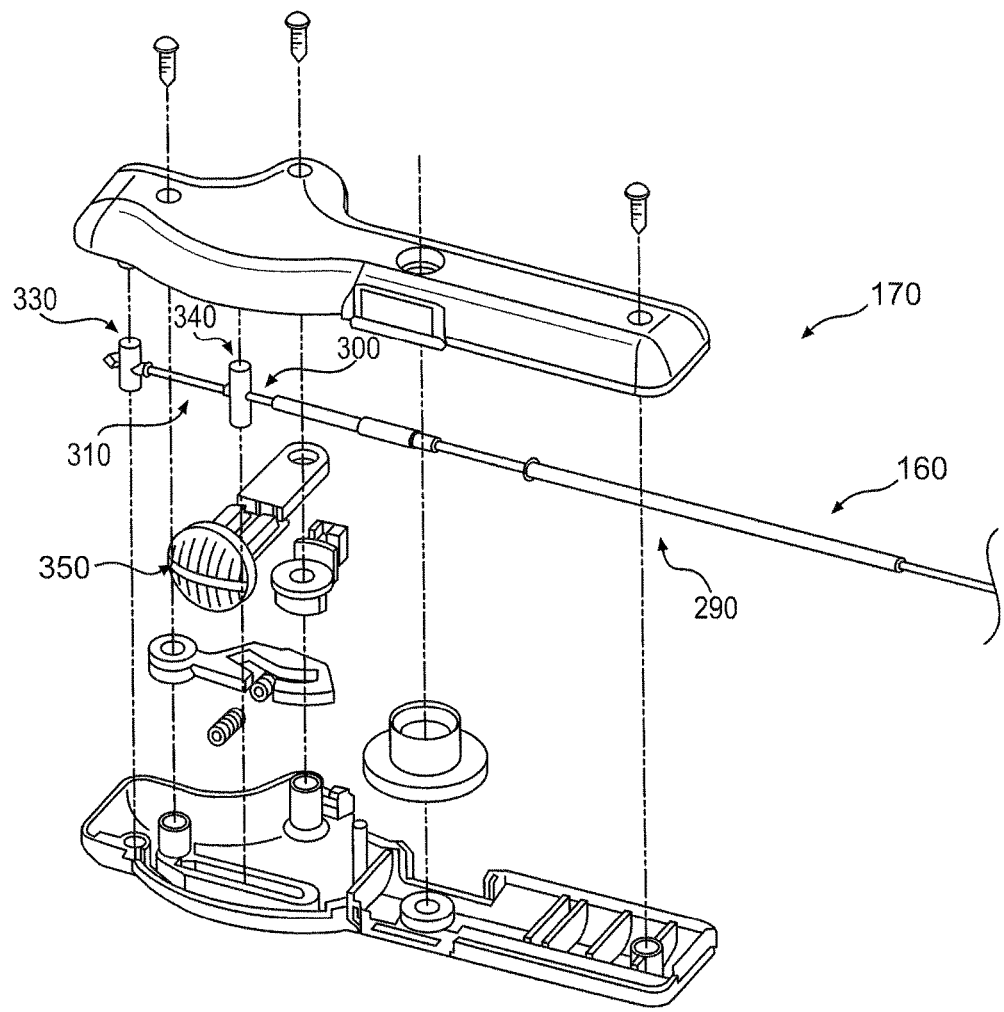
FIG. 6 is an exploded view of a portion of a controller, according to another exemplary embodiment.

As shown in FIGS. 5B and 6, inner member 310 may be attached to a pin 330 and outer member 300 may couple to a pin 340. Attachment can include fixedly attaching inner member 310 and pin 330 and moveably attaching inner member 310 and pin 330 whereby their positions relative to each other can be moved. An example of a moveable attachment would include a threaded attachment, whereby inner member 310 could include a threaded outer surface configured to be threaded into a corresponding threaded inner surface of pin 330. Coupling between outer member 300 and pin 340 can include placing these two components in contact or positioning them adjacent to each other. Coupling can be fixed or moveable. Relative movement between pin 330 and pin 340 can be provided by moving a lever 350 relative to handle 170. Consequently, lever 350 can be moved to actuate end-effector 190.

To adjust the tension of actuation member 160, the location of inner member 310 relative to pin 330 can be adjusted or the location of outer member 300 relative to pin 340 can be adjusted. For example, inner member 310 could be moved into or out of pin 330 to move inner member 310 relative to outer member 300. Such movement can be rotational, as described above, and may be used to accurately adjust a tension applied to inner member 310. It is also possible to move outer member 300 away from or toward pin 340. Such movement would vary the compressive force applied to outer member 300. Both positions of members 300, 310 relative to pins 330, 340 could also be adjusted. Other configurations of moving and stationary components within handle 170 are also contemplated to selectively pre-tension actuation member 160 depending on the type of end-effector 190 used with device 10.

In operation, control members 130 can be selectively tensioned to control elongate shaft 30. Control members 130 can be moved by selectively moving handle 170 relative to base 180. As shown in FIG. 4B, shaft 280 can couple handle 170 to base 180. To permit moveable coupling between handle 170 and base 180, controller 20 can include a pivot assembly 380 (see FIG. 8) moveably coupling shaft 280 to a frame 370 of controller 20.

Figure 7:
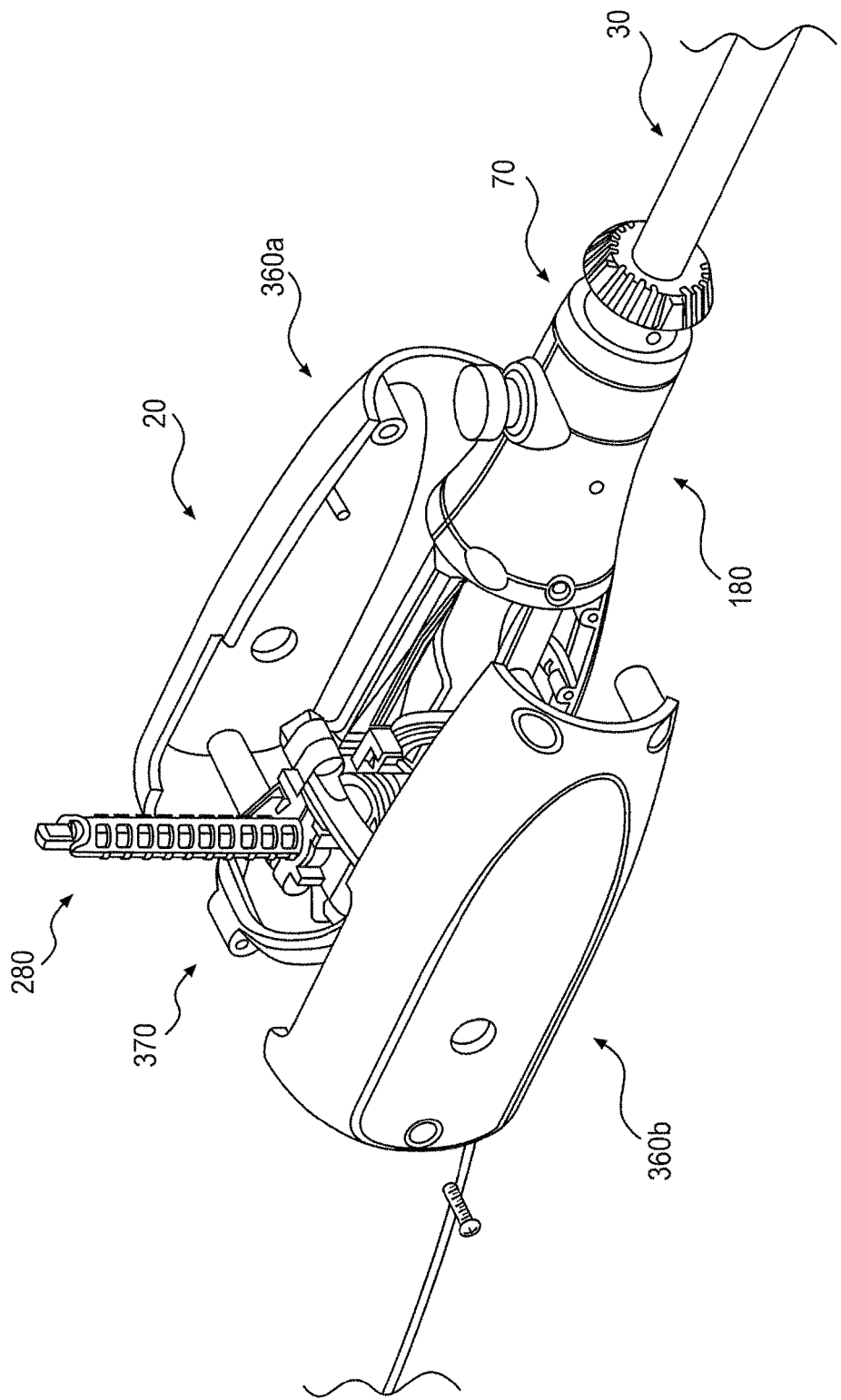
FIG. 7 is a partially exploded perspective view of a controller, according to an exemplary embodiment.

FIG. 7 depicts a partial cut-away perspective view of controller 20 without handle 170 and where outer shells 360a, 360b of controller 20 have been partially moved apart to reveal frame 370. In other embodiments, part or all of outer shells 360a, 360b could be integrally formed with frame 370. For example, base 180 and frame 370 could be a single structure formed by one molded component.

Figure 8:
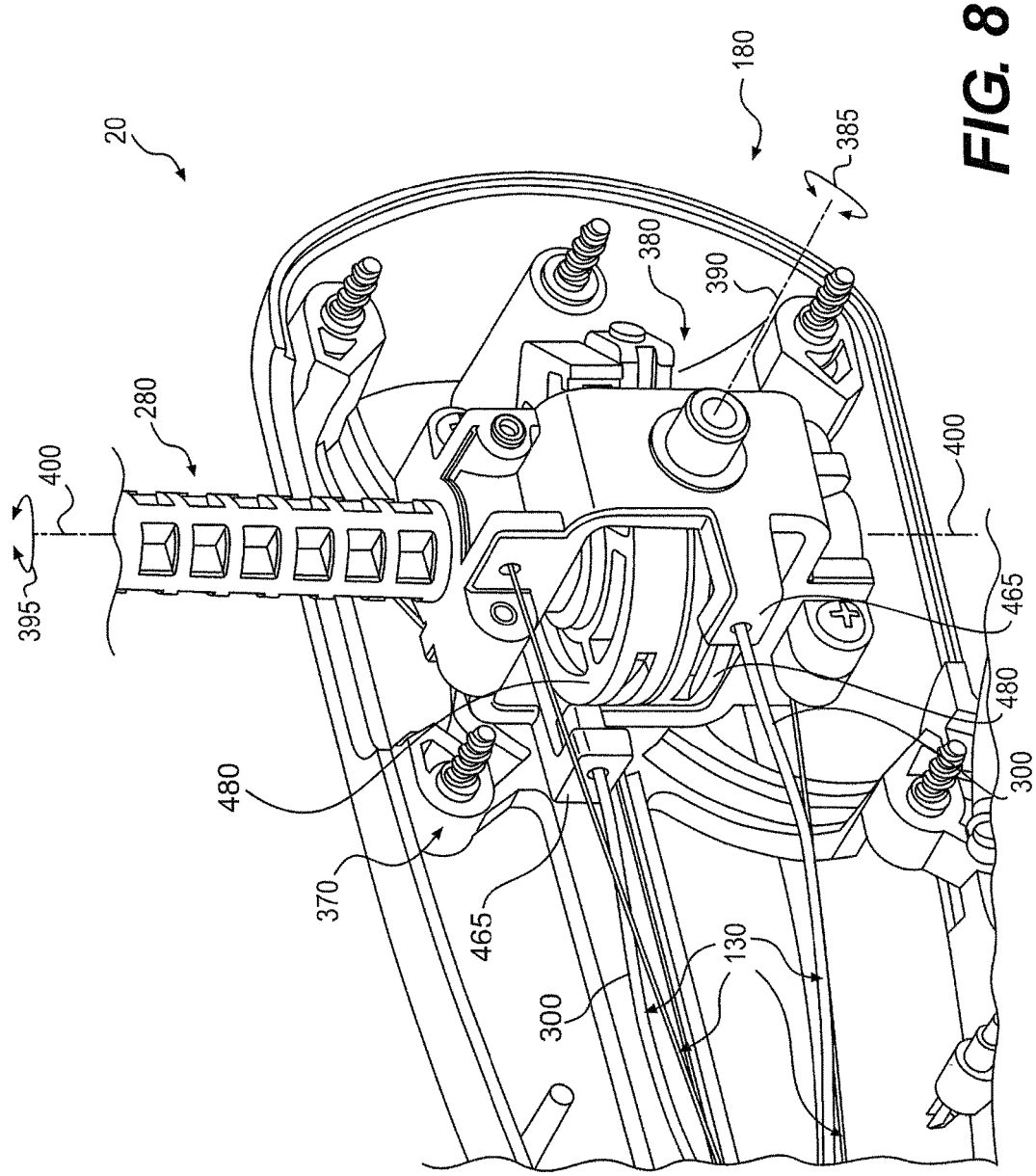
FIG. 8 is a cut-away perspective view of a proximal region of a controller, according to an exemplary embodiment.

FIG. 8 shows a cut-away view of controller 20 showing a view through frame 370 to pivot assembly 380. In other embodiments, shaft 280 may be coupled to frame 370 using a hinge, a flexible member, or other type of moveable coupling.

Shaft 280 can be configured for rotational movement about one or more axes relative to frame 370. For example, shaft 280 can be rotated forward or backwards relative to frame 370, as shown by arrow 385, by a user about a lateral axis 390 to provide up or down movement of elongate shaft 30. Shaft 280 can also be rotated relative to frame 370, as shown by arrow 395, about an shaft axis 400 located generally perpendicular to lateral axis 390 to provide left or right movement of elongate shaft 30. Forward or backward movement of a user's hand along longitudinal axis 60 may move controller 20 and elongate shaft 30 forward or backwards along longitudinal axis 60 relative to a patient (not shown). In other embodiments, different movements of shaft 280 or handle 170 can selectively move elongate shaft 30 in different directions.

Control members 130 can be coupled to pivot assembly 380, handle 170, shaft 280, trigger 200, or similar components such that movement of those components can provide movement of control members 130 relative to frame 370. Similarly, actuation member 160 could be variously coupled to one or more moveable components to selectively actuate end-effector 190. Simultaneous movement of handle 170 and trigger 200 can also be used to simultaneously control articulation and actuation of end-effector 190 with one hand.

As shown in FIG. 8, control members 130 can be coupled to pivot assembly 380. Pivot assembly 380 can provide rotational movement in one or more directions, such as, for example, about lateral axis 390 and shaft axis 400. Pivot assembly 380 could also be configured to provide rotational movement about only one axis, or three or more axes that may or may not be generally perpendicular to each other. Pivot assembly 380 may also include one or more moveable components to permit relative movement between one or more control members 130.

FIG. 9 illustrates pivot assembly 380, according to an exemplary embodiment. Pivot assembly 380 is shown including a pivot body 410 and a pulley assembly 420 coupled to shaft 280. Pivot body 410 may be moveably coupled to frame 370 (FIGS. 7 and 8). Pivot body 410 may also be moveably coupled to pulley assembly 420 or shaft 280.

FIG. 10 illustrates an exploded view of pivot assembly 380 shown in FIG. 9. As shown, pivot body 410 can include two pivot body components 430. Various attachment mechanisms may be used to fixedly attach pivot body components 430. Pivot body 410 could also be formed from a single component or multiple other components. Also, one or more of shaft 280, a drive mechanism 490, a pulley 480, or pulley assembly 420 may be combined and formed into one or more structures. For example, shaft 280, drive mechanism 490, and pulleys 480 could be formed from a single molded structure.

Pivot body component 430 can include a first rotation element 440 to allow relative movement between pivot body 410 and frame 370. Other examples of rotation element 440 include a protrusion, a recess, an elastic material, a bearing surface, or other structure configured to permit movement. Pivot body component 430 may also include a second rotation element 450 configured to permit movement between pivot body 410 and shaft 280 or pulley assembly 420. Pivot body component 430 can also include an attachment mechanism 460 configured to fixedly attach one or more control members 130 (FIG. 2) to pivot assembly 380. Pivot body component 430 can also include a control member port 465 configured to receive one or more control members 130. As shown in FIG. 8, outer member 300 of control member 130 may abut port 465 while inner member 310 (FIGS. 5A, 5B, and 6) may pass through port 465 and couple to pulley 480.

Pulley assembly 420 can be fixedly or moveably attached to shaft 280. As shown in the exploded view of pulley assembly 420 in FIG. 11, assembly 420 can include one or more washers 470, one or more pulleys 480, and drive mechanism 490. These elements can be variously arranged and coupled to shaft 280. For example, washers 470 may be located at either end of pulley assembly 420 to facilitate relative movement between one or more components.

Pulley 480 may include a generally circular profile. In other embodiments, pulley 480 could include an asymmetrical profile to deliver force in a non-linear application. For example, pulley 480 could include a cam surface (not shown) with increasing or decreasing radius of curvature. Rotating such a pulley 480 could increase a force applied to control member 130 as pulley 480 is rotated.

Drive mechanism 490 can include a collar 510 configured to engage one or more pulleys 480. Drive mechanism 490 can also include a pin 520 to fixedly attach collar 510 to shaft 280. In operation, rotational movement of drive mechanism 490 can selectively engage one or more pulleys 480. For example, clockwise movement of drive mechanism 490 may move an upper pulley 480 clockwise while a lower pulley 480 remains stationary. Counter clockwise movement of drive mechanism 490 can move the lower pulley 480 anticlockwise while the upper pulley 480 remains stationary. Drive mechanism 490 may also be fixedly coupled to one or more pulleys 480. Pulley 480 can also include an attachment mechanism 500 configured to attach to control member 130.

During manufacture of device 10, one or more control members 130 may require pre-tensioning. Pre-tensioning may include applying a known tension to control member 130. In some embodiments, all control members 130 configured for articulation may require the same tensioning, for example, 1 lb of tension. In other embodiments, one or more control members 130 may require differential tensioning, wherein a first control member 130 is tensioned to 1 lb and a second control member 130 is tensioned to 1.5 lb.

Figure 12:
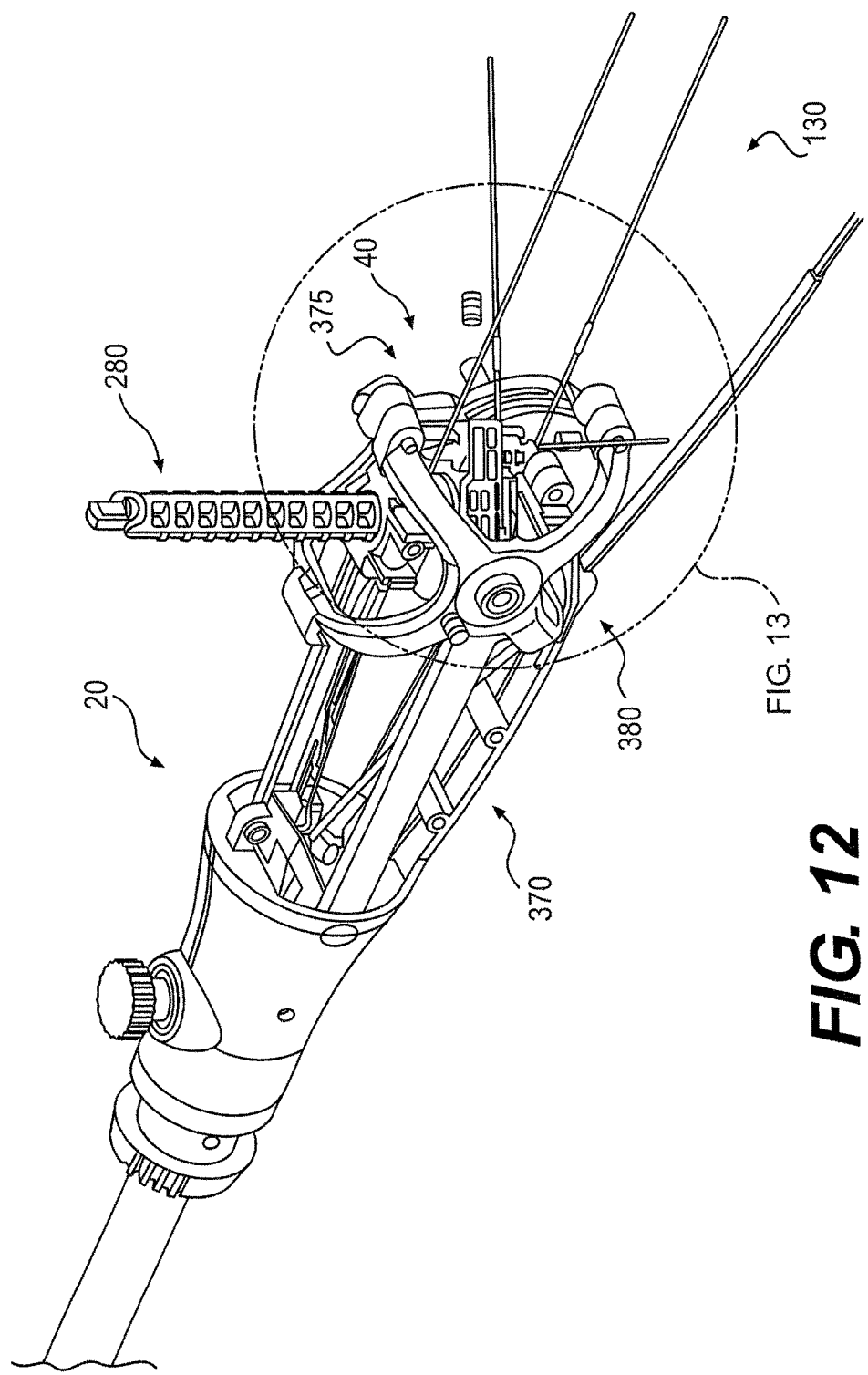
FIG. 12 is a partial cut-away perspective view of a controller, according to an exemplary embodiment.

In some embodiments, tension can be applied to control members 130 with control members 130 extended beyond proximal end 40 of device 10, as shown in FIG. 12. Specifically, control members 130 can be extended proximally beyond pivot assembly 380 and through an opening 375 in frame 370. An enlarged view of proximal end 40 is further shown in FIG. 13.

Figure 13:
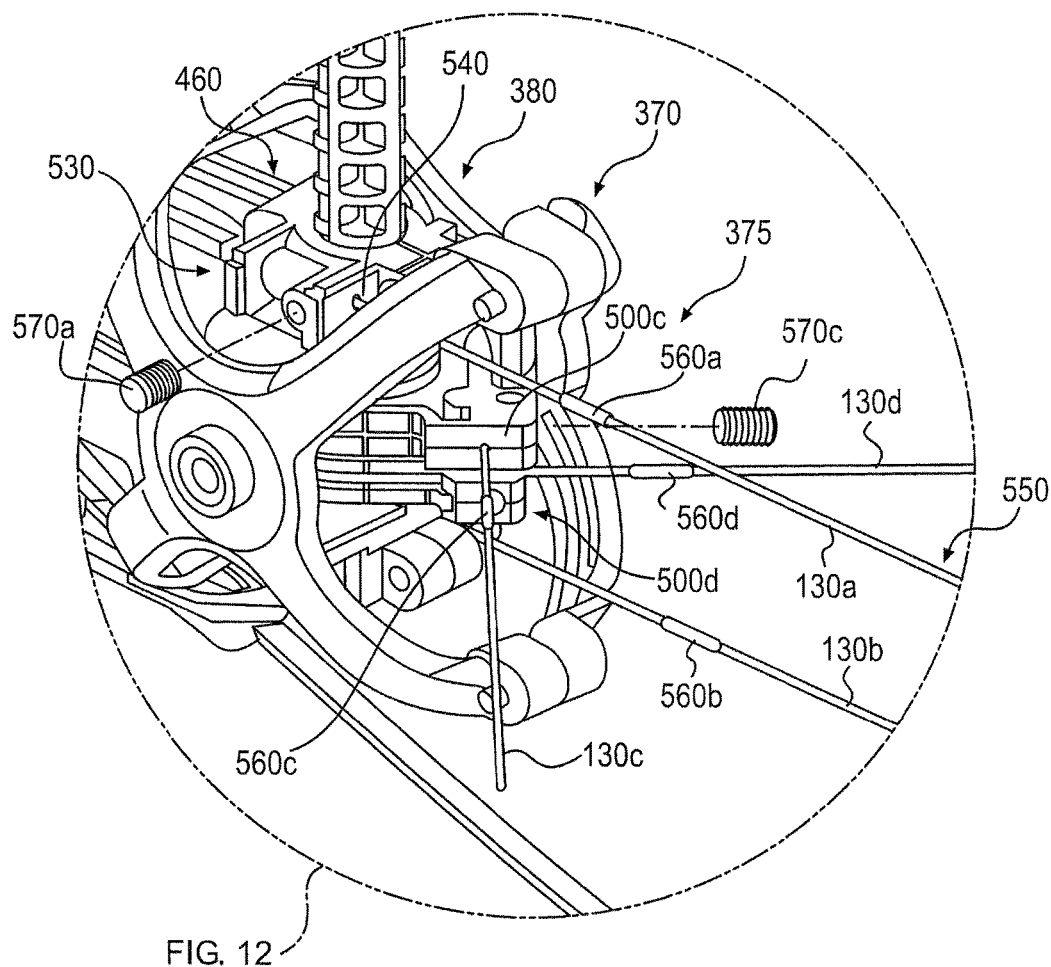
FIG. 13 is an enlarged view of the partial cut-away perspective view of the controller shown in FIG. 12.

FIG. 13 shows four control members 130a-d passing through pivot assembly 380, wherein member 130a is positioned to control upward movement, member 130b to control downward movement, member 130c to control right movement, and member 130d to control left movement of elongate shaft 30. All four control members 130a-d are shown extending beyond pivot assembly 380 through opening 375.

Attachment mechanism 460 on pivot assembly 380 can be configured to receive control member 130. Attachment mechanism 460 can include a distal end 530 and a proximal end 540. As shown in FIG. 13, a proximal end 550 of control member 130a may be passed through distal end 530 then proximal end 540 of attachment mechanism 460. With proximal end 550 extending beyond frame 370, control member 130a may be tensioned as described below. Following application of a required tension, control member 130a may be attached to attachment mechanism 460 using an attachment member 570a. Similarly, attachment member 570c may be used to attach control member 130c to attachment mechanism 500c. Attachment member 570 could include a nut, a screw, an adhesive, or other type of element configured to attach control member 130 to attachment mechanism 460, 500. In some instances, control members 130 may each include a hypotube 560a-d configured for placement about control members 130a-d and to aid attachment.

Frame 370 or pivot assembly 380 may be specifically configured to permit one or more control members 130 to extend beyond frame 370 or proximal end 40. For example, frame 370 could be "X" shaped from a lateral perspective to permit multiple control members 130 to extend proximally beyond frame 370 through opening 375. Further, attachment mechanisms 460, 500 can be configured to direct all or some control members 130 through opening 375 or another opening in frame 370. Opening 375 may also be large enough to permit access to attachment mechanisms 460, 500 to permit attachment of control members 130 to pivot assembly 380.

Figure 14:
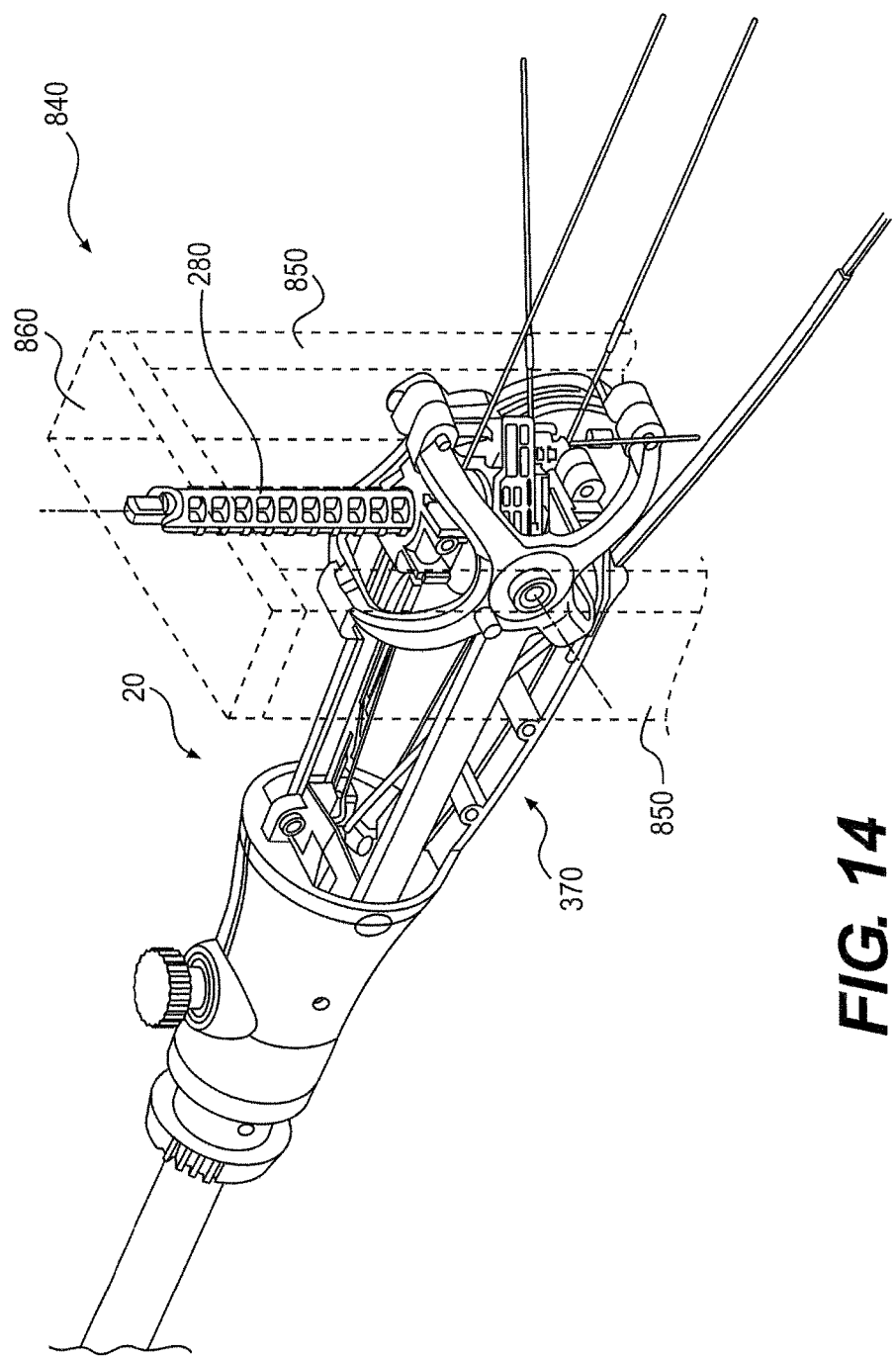
FIG. 14 is a partial cut-away perspective view of a controller and a tensioning fixture, according to an exemplary embodiment.

One or more control members 130 may be tensioned using a tensioning fixture 840. Fixture 840 is shown in FIG. 14 as transparent to indicate the positioning of fixture 840 relative to controller 20, according to an exemplary embodiment. Fixture 840 can include one or more support members 850 configured to engage frame 370 or other part of controller 20. Fixture 840 can also include a support member 860 configured to engage shaft 280.

Figure 15:
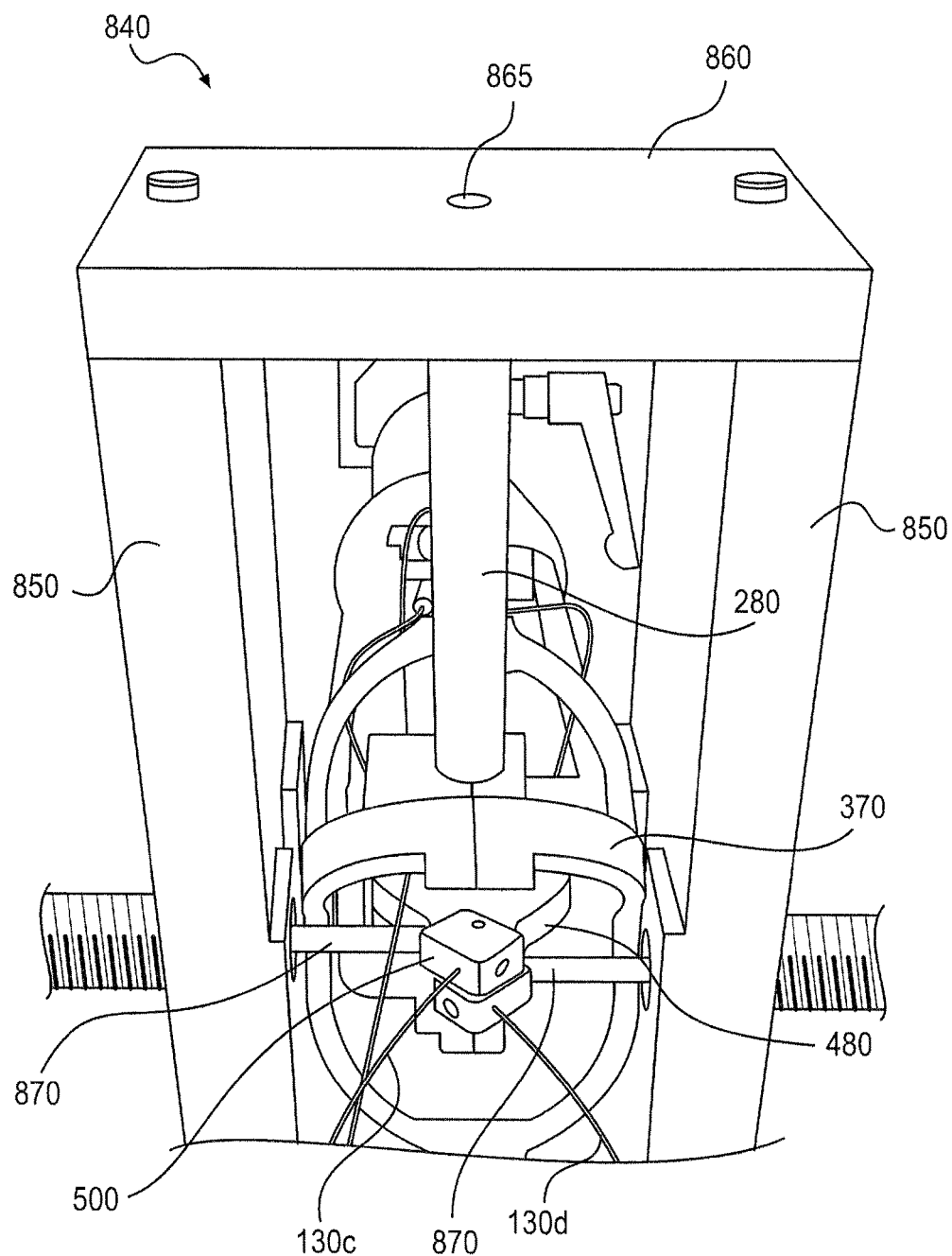
FIG. 15 is a perspective view of a controller and a tensioning fixture, according to an exemplary embodiment.
Figure 16:
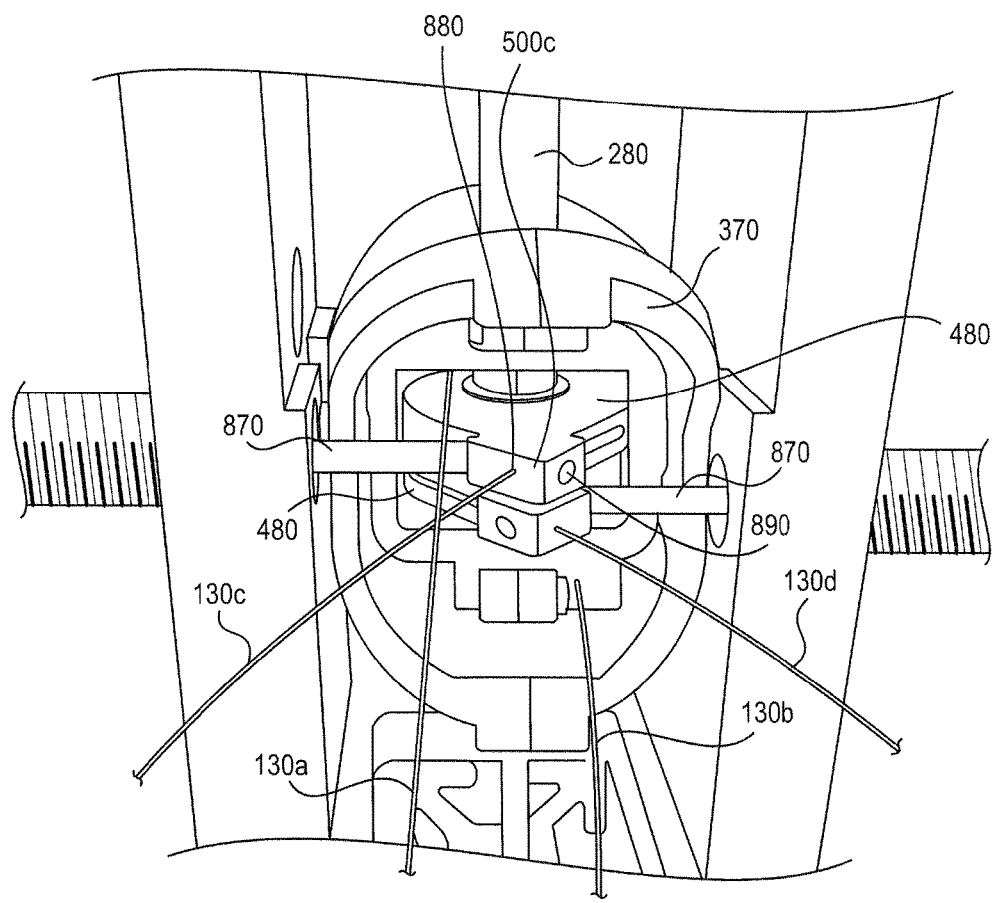
FIG. 16 is an enlarged view of the controller and the tensioning fixture shown in FIG. 15.

Once frame 370 or controller 20 is secured by fixture 840, the movement of pulley 480 may be locked. For example, as shown in FIGS. 15 and 16, a stabilizing pin 870 may be extended from support member 850 to abut pulley 480 or attachment mechanism 500. A second stabilizing pin 870 may be used to lock the position of a second pulley 480. Support member 860 can include an opening 865 configured to receive an end of shaft 280. Other devices and methods of limiting movement of one or more components of pivot assembly 380 are also contemplated.

Once shaft 280 and pulleys 480 are locked in position, other components of device 10 may require positioning. For example, elongate shaft 30, distal region 110, or steering section 140 may be straightened or placed in an appropriate neutral position.

It is contemplated that various components of device 10 can be positioned in a neutral position. The neutral position can be a configuration of device 10 where no forces are applied to controller 12. For example, no forces are applied to handle 170 or trigger 200. Device 10 can assume the neutral position during use when a surgeon's hand relaxes.

While shown with shaft 280 located perpendicular to frame 370, shaft 280 may be fixed within fixture 840 at another angle relative to frame 370. For example, shaft 280 could be located at 60 degrees relative to frame 370 in a longitudinal direction, lateral direction, or some combination.

Shaft 30 may be located in a neutral position prior to attaching control members 130 to pivot assembly 380. For example, steering section 140 may be generally straight. Fixing control members 130 when steering section 140 is generally straight can provide a neutral position for device 10 wherein shaft 30 is generally straight. If device 10 is required to have a neutral position with a non-straight shaft 30, shaft 30 could be placed in the non-straight configuration prior to fixing control members 130. Positioning end-effector 190 in an open, a closed, or another configuration prior to fixing actuation member 160 can also affect a neutral position of end-effector 190. Following appropriate alignment or positioning of various components of device 10, control members 130 may be tensioned during assembly.

To tension control member 130, a weight may be applied to control member 130. Control member 130 may also be tensioned using a spring, a load cell, an instron machine, a digital tensioner, or some other device configured to apply a known tension to one or more control members 130. Once the appropriate tension is applied to control member 130, control member 130 can be attached to attachment mechanism 460, 500.

Optionally, hypotubes 560a-d may be placed, respectively, over control members 130a-d, as shown in FIG. 13. For example, referring back to FIGS. 15 and 16, hypotube 560c can be placed over control member 130c and located within an opening 880 of attachment mechanism 500c. Once properly located within attachment mechanism 500c, hypotube 560c or control member 130c may be attached to attachment mechanism 500c by positioning attachment member 570c in an opening 890. Attachment member 570c can be configured to at least partially compress or crimp hypotube 530c to anchor control member 130c within pulley 480. Following attachment, control members 130 could be cut (not shown) just proximal to attachment mechanism 460, 500.

Actuation member 160 could also be tensioned using fixture 840 as described above and fixed relative to trigger 200. Following pre-tensioning of control members 130, control members 130 can be further tensioned or untensioned by a user. As explained above, device 10 could be stored and shipped in an untensioned state, and tensioned just prior to use. In some embodiments, device 10 can be tensioned by a user using tensioning mechanism 70.

Figure 17:
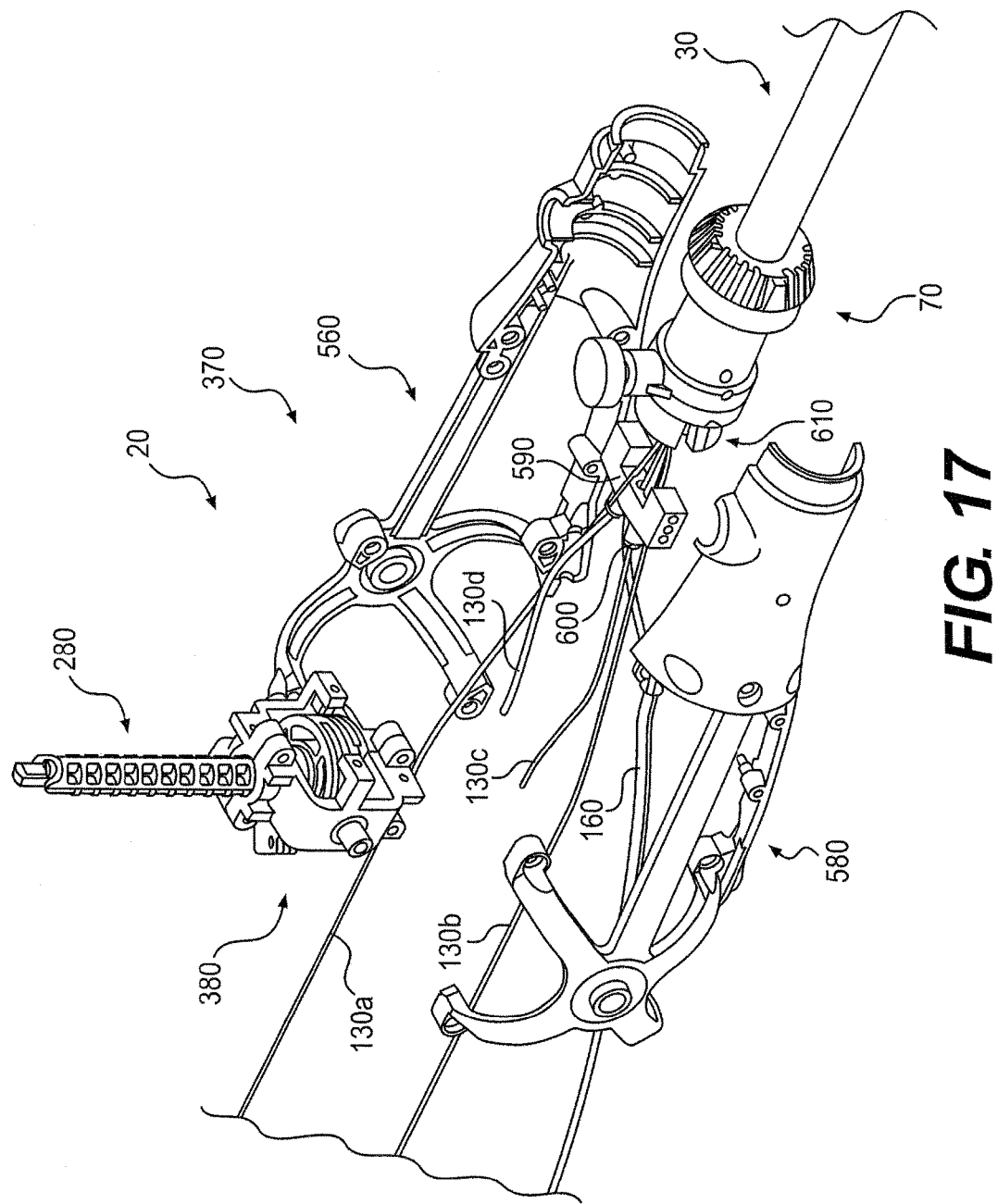
FIG. 17 is a partially exploded view of a controller, according to an exemplary embodiment.

FIG. 17 shows an exploded view of controller 20, showing frame 370 with two frame components 580. In other embodiments, frame 370 may be formed from one or more than two components. FIG. 17 also shows elongate shaft 30 and tensioning mechanism 70 located proximally along elongate shaft 30. Control members 130 are shown extending within controller 20 past pivot assembly 380. Tensioning mechanism 70 may be used to selectively tension or untension (or release tension from) one or more control members 130.

Control member 130 can include a section that includes Bowden cable 290 (FIG. 5A). FIG. 17 shows a proximal region of control members 130c, 130d with a section of Bowden cable 290, while the proximal regions of control members 130a, 130b include no Bowden cable 290. At least part of some control members 130 may include Bowden cable 290 to permit independent movement of other control members 130. While one control member 130 is moved, it may be desirable to keep another control members 130 stationary. Such independent movement of control members 130 can be achieved through the use of Bowden cables 290 because Bowden cable 290 can be flexed without moving inner member 310 relative to outer member 300. For example, control members 130c, 130d can flex while control members 130a, 130b are moved by pivot assembly 380. However, the flexible movement of control members 130c, 130d does not cause articulation of control members 130a, 130b.

Control members 130 may be directed generally distally through frame 370. One or more control members 130 including Bowden cable 290 can pass through a plate 590. In operation, plate 590 can transfer compressive forces from outer member 300 to frame 370. While only control members 130*c, d* are shown to include a proximal section of Bowden cable 290, control members 130*a, b* could also include a proximal section of Bowden cable 290.

Plate 590 can also include one or more tensioning nuts 600 (see FIG. 23) configured to engage a distal end of Bowden cable 290 of control members 130*c*, 130*d*. Nut 600 can be adjusted to adjust the relative length of inner member 310 relative to outer member 300 of the section of Bowden cable 290 to tension or untension control members 130*c*, 130*d*. In other embodiments, plate 590 may be formed as part of frame 370.

Figure 18:
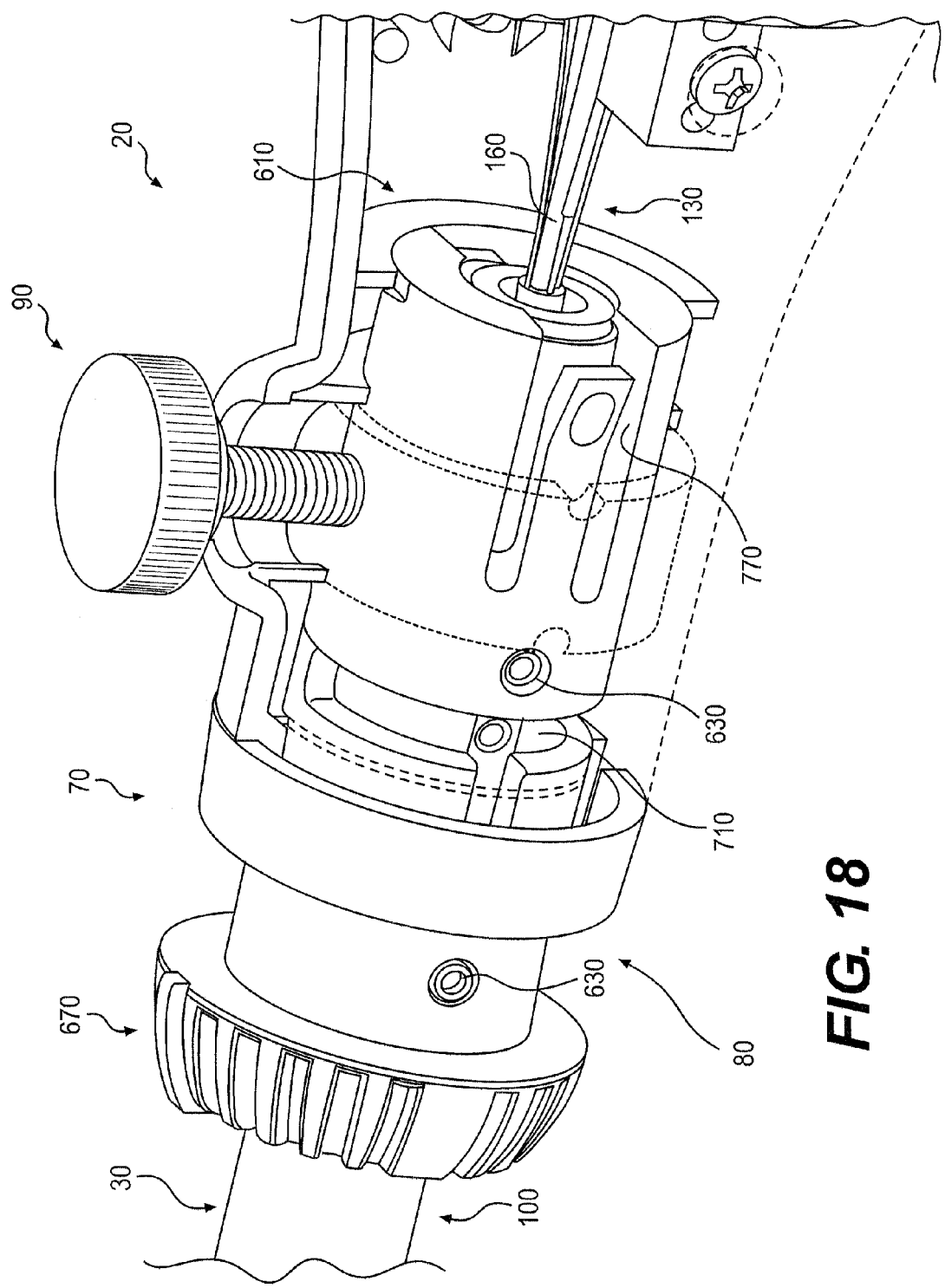
FIG. 18 is a partial cut-away perspective view of a tensioning mechanism, according to an exemplary embodiment.

FIG. 18 shows a cut-away view through tensioning mechanism 70. Control members 130, including actuation member 160, may pass through a proximal end 610 of tensioning mechanism 70. In some embodiments, tensioning mechanism 70 can include knob 80 that can be fixedly attached to proximal region 100 of elongate shaft 30. For example, one or more screws 630 could be used to attach knob 80 to proximal region 100 of elongate shaft 30.

Knob 80 can be configured to move relative to controller 20. For example, knob 80 can permit axial or rotational movement between controller 20 and elongate shaft 30. Tensioning mechanism 70 can also include rotational lock 90 configured to limit rotational movement between controller 20 and elongate shaft 30.

Figure 19:
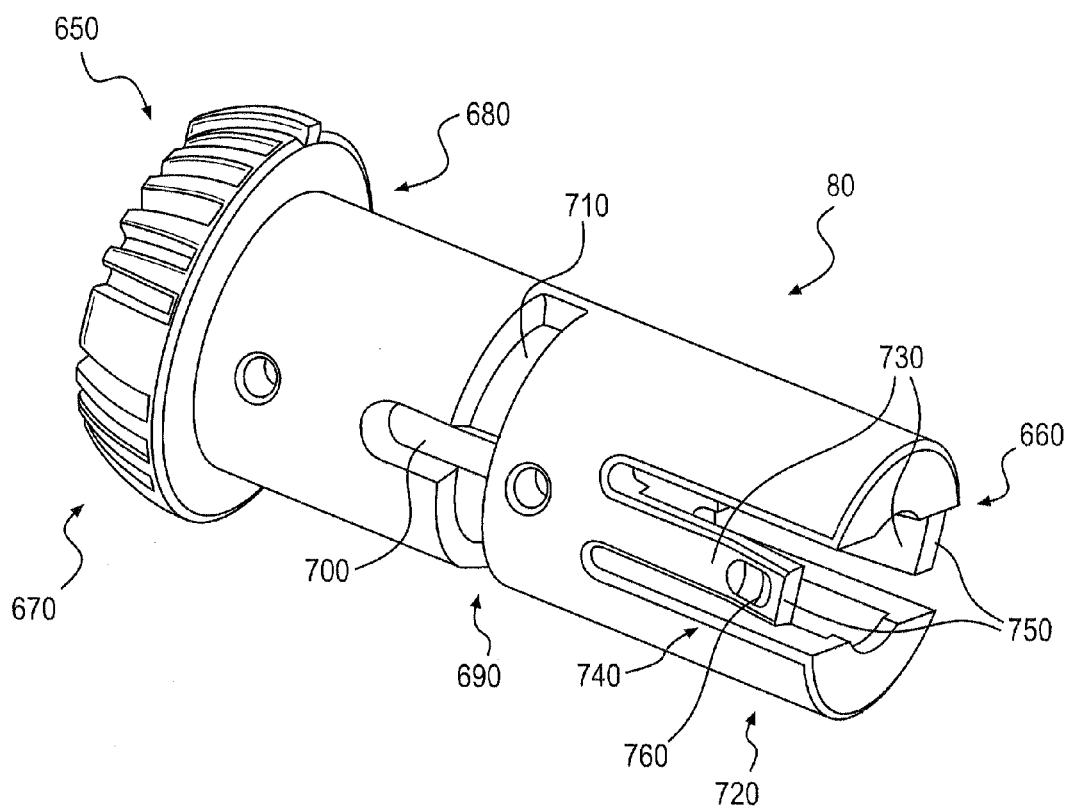
FIG. 19 is a perspective view of a tensioning mechanism, according to an exemplary embodiment.

FIG. 19 illustrates knob 80 according to an exemplary embodiment. Knob 80 can include a distal end 650 and a proximal end 660. Knob 80 can include a grip 670 to permit a user to move knob 80. While shown at distal end 650 in FIG. 19, grip 670 can be variously located along knob 80.

Figure 20:
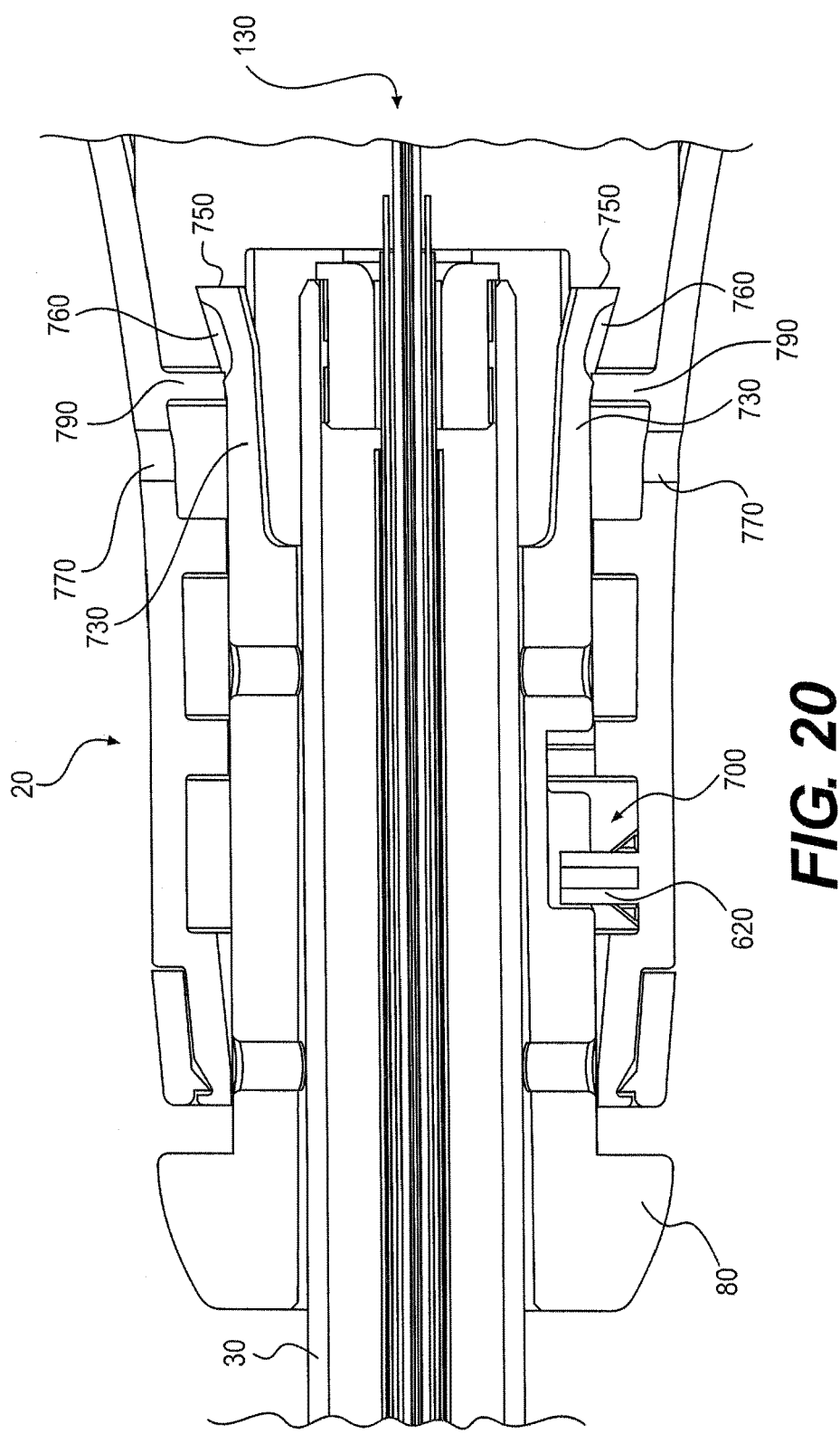
FIG. 20 is a cut-away top view of a tensioning mechanism in an untensioned configuration, according to an exemplary embodiment.

Knob 80 can include a slot 690 or similar structure configured to limit relative movement between knob 80 and controller 20. As shown in FIG. 19, slot 690 can include an axial slot 700 and a radial slot 710. Controller 20 can include a protrusion 620, as shown in FIG. 20, configured to engage slot 690. In some embodiments, protrusion 620 may only move axially within slot 700, limiting the relative axial movement between knob 80 and controller 20. Protrusion 620 may only move radially within slot 710, limiting the relative radial movement between knob 80 and controller 20. While slot 700 can be connected to slot 710, it is also contemplated that controller 20 may include multiple protrusions 620 configured to limit relative movement. In other embodiments, controller 20 could include one or more slots 690 and knob 80 could include one or more protrusions 620. Knob 80 can also include a surface 680 or other structure configured to engage a corresponding surface or structure on controller 20 to limit the relative movement between knob 80 and controller 20.

Knob 80 can also include a locking mechanism 720. Locking mechanism 720 can be configured to automatically lock movement between controller 20 and elongate shaft 30. In operation, locking mechanism 720 can allow a user to lock device 10 in the tensioned configuration by moving knob 80 distally relative to controller 20, as shown by arrow 780 in FIG. 21. For example, locking mechanism 720 can include two tabs 730 configured to expand radially to limit the movement of knob 80 relative to controller 20. Tab 730 could also include a release mechanism 740 configured to allow a use to selectively release locking mechanism 720.

When device 10 is untensioned, as shown in FIG. 20, knob 80 can be located proximally relative to controller 20. In this position, protrusion 620 can be located at a distal end of slot 700. As knob 80 is moved distally relative to controller 20 (by moving knob 80 to the left as shown in FIG. 20) to apply tension to control members 130, tabs 730 can slide past retaining members 790 fixedly attached to controller 20. Retaining members 790 can be configured to constrain the radial movement of tabs 730. After sufficient distal movement, ends 750 of tabs 730 can move past retaining members 790 and expand radially, locking device 10 in the tensioned configuration shown in FIG. 21. Any proximal movement (to the right) of proximal ends 750 will cause them to contact distal facing surface 800 of controller 20 to limit any further proximal movement of knob 80.

In some embodiments, device 10 can include marking or other indicia indicating an actual or relative tension applied to control members 130. For example, markings could indicate relative movement of tensioning mechanism 70, either axially or rotationally. Bars, numbers, letters or other indicia could be used.

Once in a tensioned configuration, release mechanism 740 can be configured to selectively unlock locking mechanism 720. While a user may not be aware of release mechanism 740, an engineer or service person could use it to untension a tensioned device. Such hidden unlocking capabilities could be used selectively to unlock device 10 without a typical user appreciating that device 10 could be unlocked once tensioned. The functionality of one or more components of tensioning mechanism 70 may also be hidden or not readily apparent to a surgeon or operator.

Release mechanism 740 can include a surface 760 configured to receive an object, such as a pin, passed through an aperture 770 of controller 20. In the tensioned configuration shown in FIG. 21, apertures 770 may align with surfaces 760. Simultaneously forcing both tabs 730 inward can permit knob 80 to move proximally into the untensioned configuration shown in FIG. 20. As shown, both tabs 730 should be moved inward to activate release mechanism 740. In other embodiments, one or more than two tabs 730, or similar structures, could be used.

Figure 21:
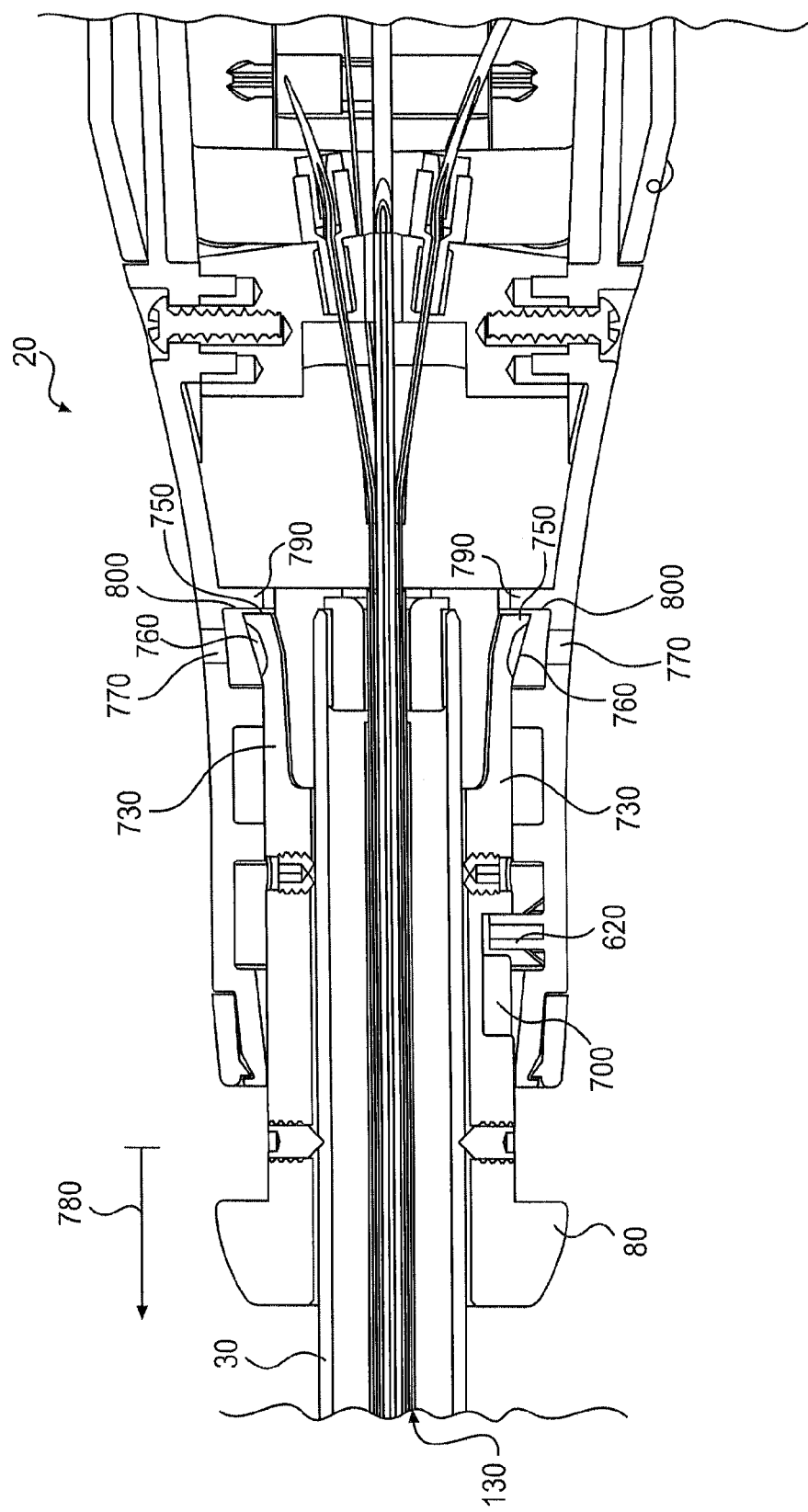
FIG. 21 is a cut-away top view of a tensioning mechanism in a tensioned configuration, according to an exemplary embodiment.

In the tensioned configuration shown in FIG. 21, knob 80 and elongate shaft 30 can be rotated relative to controller 20. With protrusion 620 positioned within slot 710 (see FIG. 19), knob 80 can selectively rotate while protrusion 620 moves radially within slot 710. Although the embodiment shown in FIG. 19 shows slot 710 allowing rotation about 180 degrees, slot 710 may be configured to permit rotation about 360 degrees or another angle.

Figure 22:
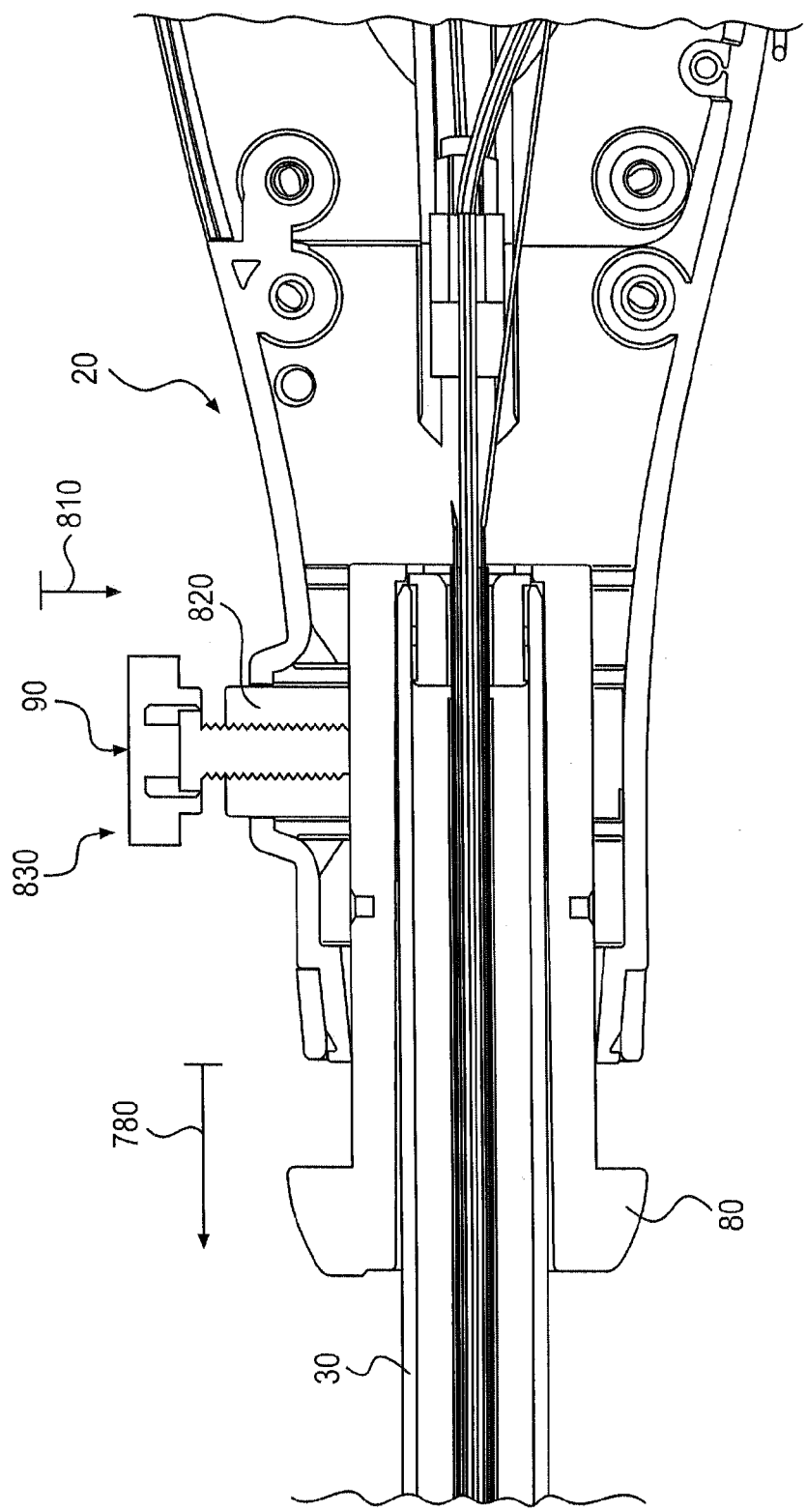
FIG. 22 is a cut-away side view of a tensioning mechanism in a tensioned configuration, according to an exemplary embodiment.

To lock rotational movement of knob 80 in the tensioned configuration, rotational locking mechanism 90 may be moved as shown by arrow 810 in FIG. 22. Rotational locking mechanism 90 can include a collar 820 and a thumb screw 830 configured to move within collar 820 to limit movement of knob 80 relative to controller 20.

One or more crush ribs (not shown) could be located about collar 820 and configured to elastically or plastically deform to limit movement between shaft 30 and controller 20. For example, a crush rib could include a plastic material and could prevent wobble between knob 80 and controller 20. The crush rib could deform when thumb screw 30 is tightened onto knob 80. One or more crush ribs located between knob 80 and controller 20 could limit axial or radial movement between these components. These or other structures could be used to limit unwanted movement between controller 20 and shaft 30.

In moving device 10 from the untensioned configuration shown in FIG. 20 to the tensioned configuration shown in FIG. 21, one or more control members 130 may be selectively tensioned. Specifically, the distal movement of knob 80 and elongate shaft 30 relative to controller 20 can tension control members 130. In some embodiments, actuation member 160 could also be tensioned.

Figure 23:
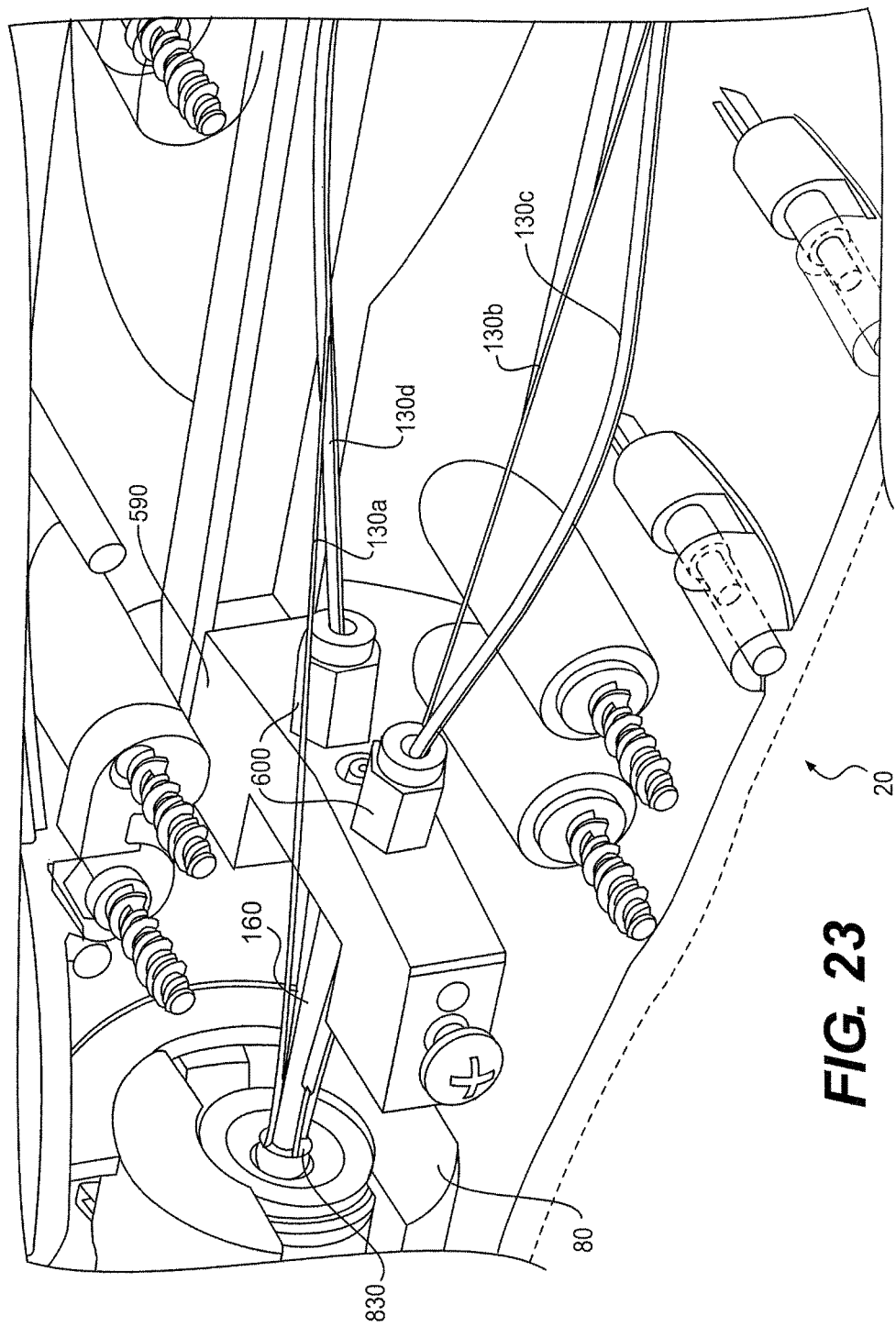
FIG. 23 is a cut-away perspective view of a controller, according to an exemplary embodiment.

FIG. 23 illustrates a cut-away perspective view of controller 20 and a proximal end 830 of elongate shaft 30 located within knob 80. As shown, device 10 is in a tensioned state and control members 130*a*, 130*b* extend from proximal end 830 to pivot assembly 380 (not shown). Control members 130*c*, 130*d* extend from proximal end 830 to plate 590. Each control member 130*c*, 130*d* passes through plate 590 and through nut 600. Nut 600 can be selectively tensioned to increase or decrease the tension applied to control members 130*c*, 130*d*.

To tension control members 130*a-d*, knob 80 can be moved distally, as described above. This distal movement lengthens the distance between elongate shaft 30 and controller 20. In particular, the distance between proximal end 830 and pivot assembly 380 is increased, which tensions control members 130*a*, 130*b*. The distal movement also increases the distance between proximal end 830 and plate 590, which tensions control members 130*c*, 130*d*. Selective tensioning of control members 130*c*, 130*d* allows control members 130*c*, 130*d* to remain flexible between plate 590 and pivot assembly 380.

Figure 24A:
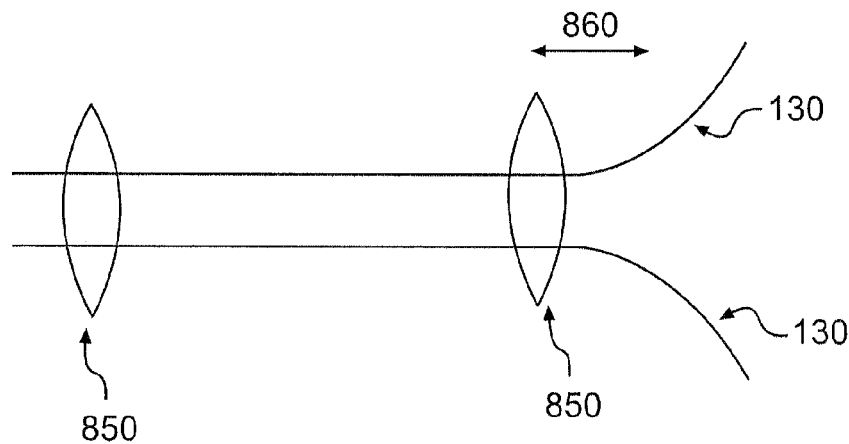
FIG. 24A is a schematic view of a tensioning mechanism, according to an exemplary embodiment.

Other ways of tensioning control members 130 are also contemplated. For example, instead of moving controller 20 relative to elongate shaft 30, a path traveled by control member 130 through controller 20 or elongate shaft 30 could be altered. For example, one or more loops 950 could be placed about one or more control members 130, as shown in FIG. 24A. One or more loops 950 may then be moved axially, as shown by arrow 960, to increase or decrease the path traveled of control members 130. Increasing the path traveled can add tension to control member 130 and decreasing the path traveled can untension control member 130.

Figure 24B:
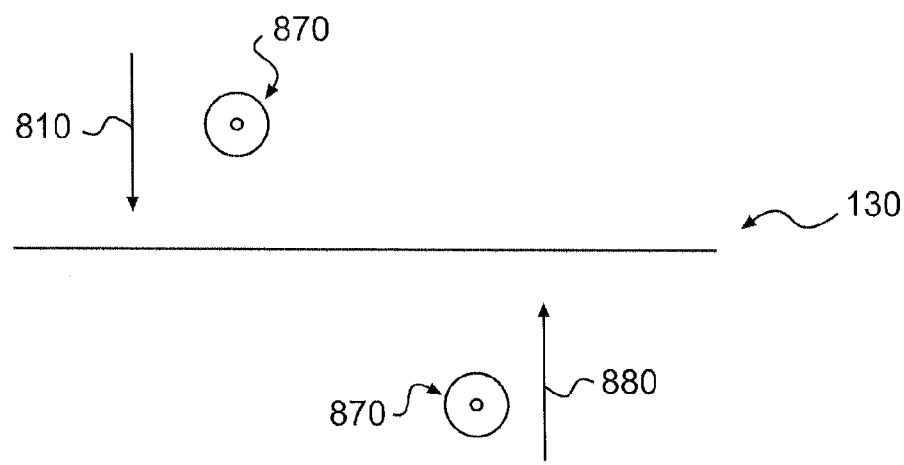
FIG. 24B is a schematic view of another tensioning mechanism, according to an exemplary embodiment.

In another embodiment, as shown in FIG. 24B, one or more pulleys 970 could be placed in contact with one or more control members 130. To tension control member 130, pulley 970 could be moved as indicated by arrow 980 to lengthen the path traveled by control member 130. Movement of pulley 970 could be lateral, axial, or a combination. In some embodiments, an idler pulley (not shown) may be used.

Figure 24C:
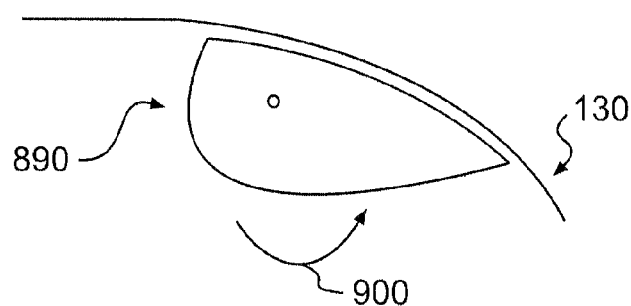
FIG. 24C is a schematic view of another tensioning mechanism, according to an exemplary embodiment.

FIG. 24C shows a cam 990 in contact with control member 130. To lengthen a path traveled by control member 130, cam 990 could be rotated anticlockwise, as shown by arrow 995. To decrease the path traveled, and untension control member 130, cam 990 could be rotated clockwise. It is also contemplated that various components for tensioning device 10 described herein may be combined or modified by one of ordinary skill.

Other locking mechanisms operable with device 10 could include a lever, a cam lock, a rack and pawl, a knob, a worm gear, or other components configured to limit relative movement. Moreover, the locking mechanisms described herein could be biased to automatically lock or unlock. It is also contemplated that tensioning mechanism 70 could be biased. For example, a release button (not shown) could be used to unlock a biasing member, such as, for example, a spring. Button depression could release the biasing member, automatically moving tensioning mechanism 70 from an untensioned to a tensioned configuration. In other embodiments, a biased tensioning mechanism 70 could be configured to tension device 10 upon removal from packaging. Device 10 may also lack release mechanism 740 or other components described herein. Proximal movement of tensioning mechanism 70 could also tension one or more control members 130.

Tensioning mechanism 70 could also be configured to selectively tension one or more control members 130. For example, tensioning mechanism 70 could include two or more knobs (not shown). These knobs could be similar to knob 80, coaxially aligned relative to each other, independently operated, or operatively associated with different control members 130. Moving a first knob may tension or untension a first set of control members 130, such as, for example, control members 130 controlling up/down movement of elongate shaft 30. Moving a second knob may tension or untension a second set of control members 130, different to the first set, that control left/right movement. Selective tensioning can provide various control members 130 with different tensions.

In another embodiment, tensioning mechanism 70 could include knob 80 with two or more moveable components (not shown), wherein each moveable component can be operatively associated with one or more control members 130. As described above with the two or more knobs, these moveable components could be configured to selectively tension one or more control members 130 to different tensions.

Tensioning mechanism 70 could also include a ratcheting mechanism (not shown), or similar component, to permit different tensioning of one or more control members 130. For example, knob 80 with the ratcheting mechanism could be extended a first distance to apply a first tension to control member 130. Knob 80 could also be extended further, to a second distance, to apply a second tension to control member 130. Movement of knob 80 over different distances can provide one or more control members 130 with different tensions.

Other mechanisms to selectively control tensioning of control members 130 are also contemplated. These mechanisms could also be combined with various embodiments of tensioning mechanism 70 described herein. For example, one coaxial knob described above could be provided with a ratcheting mechanism while another coaxial knob may lack any type of ratcheting mechanism.

Other embodiments will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
  a shaft having a distal end;
  a controller coupled to the shaft;
  a control member extending through at least part of the shaft and at least part of the controller, wherein the control member in a tensioned configuration is moveable by the controller to control the distal end of the shaft, and the control member is slack in an untensioned configuration, wherein the controller circumscribes the control member and a longitudinal axis of the shaft; and
  a tensioning mechanism configured to slide along the longitudinal axis the shaft and a longitudinal axis of the controller to tension the control member, and lock the control member in the tensioned configuration.

2. The medical device of claim 1, wherein an entirety of the tensioning mechanism is slidable at the same time and in the same direction along the longitudinal axis of the shaft and the longitudinal axis of the controller to transition the control member from the untensioned configuration to the tensioned configuration.

3. The medical device of claim 2, wherein the tensioning mechanism is rotatable about the longitudinal axis in the tensioned configuration.

4. The medical device of claim 3, further including a rotational locking mechanism configured to limit the rotational movement of the tensioning mechanism.

5. The medical device of claim 1, wherein the tensioning mechanism is configured to selectively unlock to permit movement of the tensioning mechanism to transition the control member from the tensioned configuration to the untensioned configuration.

6. The medical device of claim 1, wherein the tensioning mechanism includes a rotation knob fixedly coupled to a proximal region of the shaft, and is moveably coupled to the controller to permit axial and rotational movement between the shaft and the controller.

7. The medical device of claim 6, wherein the rotation knob includes an axial locking mechanism configured to lock the rotation knob in a distal position relative to the controller.

8. The medical device of claim 7, wherein the axial locking mechanism includes a tab having a surface aligned with an aperture in an outer wall of the controller, and wherein the surface is moveable to release the rotation knob from the distal position to permit proximal movement of the rotation knob to unlock the tensioning mechanism.

9. The medical device of claim 1, wherein the tensioning mechanism includes at least one of a pulley, a cam, and a loop structure.

10. The medical device of claim 1, further including a second control member that passes through the tensioning mechanism and operates independently of the tensioning mechanism.

11. The medical device of claim 10, wherein the control member includes an articulation control member, and the second control member includes an actuation control member.

12. The medical device of claim 11, wherein the distal end of the shaft includes an end-effector, and the controller includes a trigger configured to move the actuation member to control the end-effector.

13. The medical device of claim 1, wherein at least part of the control member includes a Bowden cable.

14. The medical device of claim 13, further including a plate fixedly attached to the controller and a pivot assembly moveably coupled to the controller, wherein the Bowden cable extends from the plate to the pivot assembly.

15. The medical device of claim 1, wherein the controller is coupled to a rigid proximal region of the shaft, and the proximal region includes a disabling mechanism configured to disable movement of the tensioning mechanism.

16. The medical device of claim 1, wherein the controller includes:
a base coupled to the shaft;
a handle moveably coupled to the base and configured to move the control member to control the distal end of the shaft; and
a pivot assembly coupling the handle to the base and including a pulley, wherein the pulley comprises:
an attachment mechanism configured to attach the control member to the pulley and permit a proximal region of the control member to extend proximally beyond the pulley; and
a surface configured to receive a stabilizing member, wherein the stabilizing member is positionable against the surface to limit movement of the pulley relative to the base and permit application of a select tension to the control member prior to attaching the control member to the pulley.

17. The medical device of claim 16, wherein the attachment mechanism extends proximally from the pulley.

18. The medical device of claim 16, wherein the attachment mechanism includes a first aperture configured to receive the control member, and a second aperture configured to receive an attachment member to attach the control member to the pulley.

19. The medical device of claim 18, wherein the control member includes a hypotube, the first aperture is configured to receive the hypotube, and the attachment member is configured to at least partially compress the hypotube to attach the control member to the pulley.

20. The medical device of claim 16, wherein the base is positionable within a tensioning fixture that includes an aperture configured to receive the stabilizing member.

21. The medical device of claim 1, further including an end effector at the distal end of the shaft, wherein the control member is configured to control actuation of the end effector or articulation of the shaft.

22. The medical device of claim 21, wherein, while the control member is slack in the untensioned configuration, the control member is not operable to control actuation of the end effector or articulation of the distal end of the shaft.

23. The medical device of claim 1, wherein the control member is subjected to less force while in the untensioned configuration than while in the tensioned configuration.

24. The medical device of claim 1, wherein the tensioning mechanism is configured to move the control member between the untensioned configuration and the tensioned configuration.

25. The medical device of claim 1, further including an end effector having two jaw members movable relative to one another at the distal end of the shaft, wherein the control member is configured to control opening and closing of the jaw members and, while the control member is slack in the untensioned configuration, the control member is not operable to control the opening and closing of the jaw members.

26. A medical device, comprising:
a shaft having a distal end;
a controller coupled to the shaft;
a wire or cable extending through at least part of the shaft and at least part of the controller, wherein the wire or cable in a tensioned configuration is moveable by the controller to control the distal end of the shaft, and the wire or cable is slack in an untensioned configuration, wherein the controller circumscribes the wire or cable and a longitudinal axis of the shaft; and
a housing configured to slide along the longitudinal axis of the shaft and a longitudinal axis of the controller to tension the wire or cable, and lock the wire or cable in the tensioned configuration.

27. A medical device, comprising:
a shaft having a distal end;
a controller coupled to the shaft;
a wire or cable extending through at least part of the shaft and at least part of the controller, wherein the wire or cable in a tensioned configuration is moveable by the controller to control the distal end of the shaft, and the wire or cable is slack in an untensioned configuration, wherein the controller completely surrounds a portion of the wire or cable, and a portion of a longitudinal axis of the shaft; and
a housing configured to slide along the longitudinal axis of the shaft and a longitudinal axis of the controller to tension the wire or cable, and lock the wire or cable in the tensioned configuration.

* * * * *